(12) United States Patent
Miyazawa et al.

(10) Patent No.: US 9,030,204 B2
(45) Date of Patent: May 12, 2015

(54) SENSOR DEVICE

(75) Inventors: Takao Miyazawa, Shimosuwa-machi (JP); Juri Kato, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 93 days.

(21) Appl. No.: 13/525,695

(22) Filed: Jun. 18, 2012

(65) Prior Publication Data

US 2013/0009647 A1 Jan. 10, 2013

(30) Foreign Application Priority Data

Jul. 7, 2011 (JP) ................................. 2011-150565

(51) Int. Cl.
| | |
|---|---|
| G01R 29/12 | (2006.01) |
| G01N 27/02 | (2006.01) |
| G01R 27/08 | (2006.01) |
| G01N 17/04 | (2006.01) |
| G01R 31/04 | (2006.01) |

(52) U.S. Cl.
CPC .............. *G01N 27/021* (2013.01); *G01R 27/08* (2013.01); *G01N 17/04* (2013.01); *G01R 29/12* (2013.01)

(58) Field of Classification Search
CPC ......... G01R 27/08; G01R 29/12; G01N 27/26
USPC .......................................... 324/357, 358, 457
See application file for complete search history.

(56) References Cited

U.S. PATENT DOCUMENTS

| | | | | |
|---|---|---|---|---|
| 4,194,138 A | * | 3/1980 | Johansson et al. ................. 313/3 |
| 5,412,867 A | * | 5/1995 | Aikawa et al. .................. 29/825 |
| 6,258,431 B1 | * | 7/2001 | Reis et al. ....................... 428/63 |
| 6,683,463 B2 | * | 1/2004 | Yang et al. ..................... 324/700 |
| 7,385,295 B2 | * | 6/2008 | Son et al. ....................... 257/776 |
| 2003/0011387 A1 | * | 1/2003 | Trejo et al. ..................... 324/700 |
| 2004/0118682 A1 | * | 6/2004 | Murray et al. ................. 204/418 |
| 2006/0292848 A1 | * | 12/2006 | Park et al. ...................... 438/597 |
| 2007/0176161 A1 | * | 8/2007 | Seo et al. ......................... 257/13 |
| 2009/0058784 A1 | * | 3/2009 | Shin et al. ......................... 345/96 |
| 2011/0012628 A1 | * | 1/2011 | Dobashi et al. ............... 324/700 |
| 2011/0108399 A1 | * | 5/2011 | Furuta et al. .................. 200/181 |

FOREIGN PATENT DOCUMENTS

| | | | |
|---|---|---|---|
| JP | 58-019482 | A | 2/1983 |
| JP | 62-199784 | A | 9/1987 |
| JP | 01-084056 | U | 6/1989 |
| JP | 03-251756 | A | 11/1991 |
| JP | 06-222033 | A | 8/1994 |
| JP | 09-329568 | A | 12/1997 |
| JP | 10-221292 | A | 8/1998 |

(Continued)

*Primary Examiner* — Jermele M Hollington
*Assistant Examiner* — Raul Rios Russo
(74) *Attorney, Agent, or Firm* — Global IP Counselors, LLP

(57) ABSTRACT

A sensor device includes a first electrode, a second electrode, a gap forming member and a functional element. The first electrode is composed of a first metallic material. The second electrode is spaced apart from the first electrode, and composed of a second metallic material. The gap forming member is arranged with a gap being formed between the gap forming member and a portion of a surface of the first electrode. The functional element is configured and arranged to measure a difference in electric potential between the first electrode and the second electrode so that a state of a measurement site to be measured is measured based on the difference in electric potential as measured by the functional element.

16 Claims, 15 Drawing Sheets

(56) References Cited

FOREIGN PATENT DOCUMENTS

| | | | |
|---|---|---|---|
| JP | 11-270860 A | 10/1999 |
| JP | 2000-192265 A | 7/2000 |
| JP | 2000-192266 A | 7/2000 |
| JP | 2002-180276 A | 6/2002 |
| JP | 2005-227069 A | 8/2005 |
| JP | 2007-024872 A | 2/2007 |
| JP | 2008-164467 A | 7/2008 |
| JP | 2008-209180 A | 9/2008 |
| JP | 2008-292408 A | 12/2008 |
| JP | 2010-138686 A | 6/2010 |

* cited by examiner

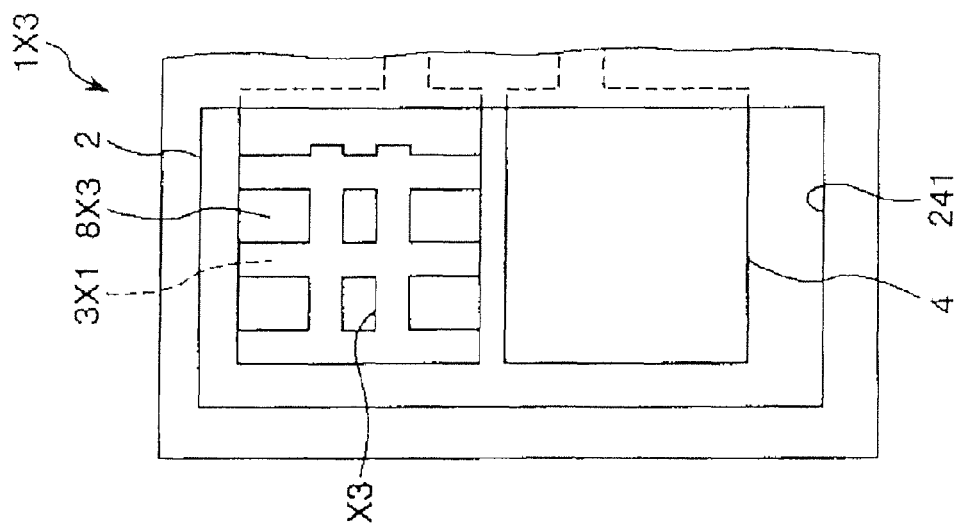
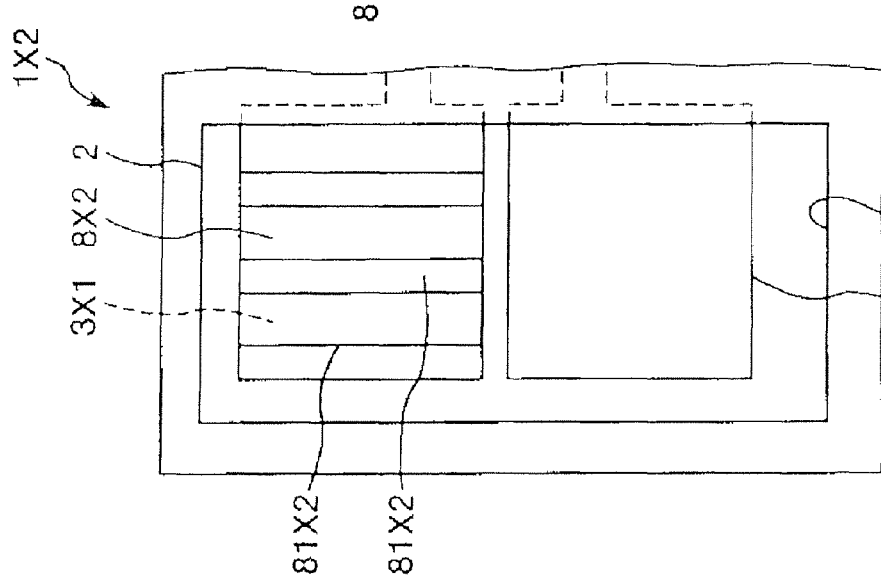
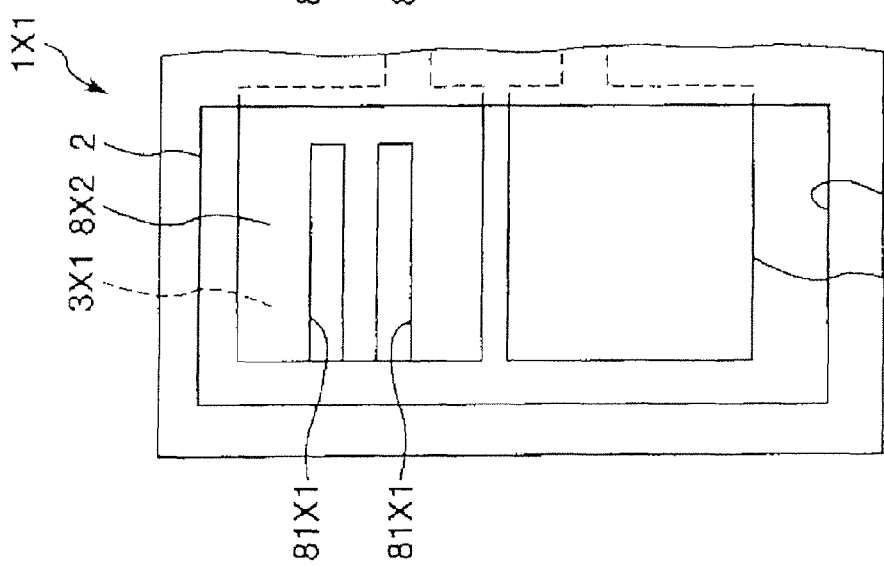

SENSOR DEVICE

CROSS-REFERENCE TO RELATED APPLICATIONS

This application claims priority to Japanese Patent Application No. 2011-150565 filed on Jul. 7, 2011. The entire disclosure of Japanese Patent Application No. 2011-150565 is hereby incorporated herein by reference.

BACKGROUND

1. Technical Field

The present invention relates to a sensor device.

2. Related Art

There are known sensor devices which, for example, measure the state of corrosion of a reinforcing bar in concrete (e.g., see Japanese Laid-Open Patent Application Publication No. H06-222033).

Typically, the concrete in a concrete structure immediately after construction exhibits a strong alkalinity. For this reason, the reinforcing bars in a concrete structure immediately after construction have a passivation film formed on the surface thereof and are therefore stable. However, in a concrete structure that is affected after construction by acid rain, exhaust gas, and the like, the concrete will be gradually acidified (neutralization), and the reinforcing bars will therefore corrode. With concrete structures, the reinforcing bars also corrode due to chloride ions that infiltrate the concrete.

For example, in the device recited in the above mentioned publication, a probe provided with a reference electrode and a counter electrode is embedded in concrete and measures the polarization resistance and changes in electric potential caused by the corrosion of the reinforcing bars, whereby the corrosion of the reinforcing bars is predicted.

However, with this device, it is not possible to identify whether the cause of the corrosion of the reinforcing bars is due to chloride ions that infiltrate the concrete or due to neutralization of the concrete, and as a result, there is the problem that it is not possible to perform suitable preservation of the concrete structure.

SUMMARY

An objective of the present invention is to provide a sensor device with which it is possible to distinguish between and measure chloride ion concentration changes and concrete pH changes in the concrete of a concrete structure, and to use the resulting measurement information in planning the preservation of the concrete structure.

Such an objective is achieved by the present invention described below.

A sensor device according to one aspect of the present invention includes a first electrode, a second electrode, a gap forming member and a functional element. The first electrode is composed of a first metallic material. The second electrode is spaced apart from the first electrode, and composed of a second metallic material. The gap forming member is arranged with a gap being formed between the gap forming member and a portion of a surface of the first electrode. The functional element is configured and arranged to measure a difference in electric potential between the first electrode and the second electrode so that a state of a measurement site to be measured is measured based on the difference in electric potential as measured by the functional element.

According to the sensor device having such a configuration, a gap is formed locally between the first electrode and the gap forming member, so even when the chloride ion concentration of the site to be measured is in a relatively low state for which corrosion of the second electrode will not occur, it is possible to have corrosion of the first electrode occur using the gap corrosion.

For that reason, even when the chloride ion concentration of the site to be measured is in a relatively low state, a difference in electric potential occurs between the first electrode and the second electrode, and it is possible to detect infiltration of chloride ions based on this difference in electric potential.

In the sensor device according to the above described aspect of the present invention, each of the first metallic material and the second metallic material is preferably a metallic material in which a passivation film is formed on a surface thereof or an existing passivation film on the surface thereof is eliminated in association with environmental changes in the measurement site.

Thereby, when the pH of the site to be measured is a prescribed value or greater, the passivation film is formed on the surface of the first electrode and the second electrode.

Here, the passivation film formed on the second electrode is not destroyed until the chloride ion concentration of the site to be measured is relatively high, and even if local damage occurs temporarily, it is regenerated in an environment for which the pH is a prescribed value or higher. For that reason, when the pH of the site to be measured is a prescribed value or higher, during the time until the chloride ion concentration of the site to be measured becomes relatively high, a state for which the self-potential of the second electrode is high (more noble state) is maintained with stability.

Meanwhile, with the passivation film formed on the first electrode, when local destruction occurs temporarily due to chloride ions that infiltrate between the first electrode and the gap forming member even when the chloride ion concentration of the site to be measured is relatively low, within that gap, the concentration of metal ions eluted from the first electrode increases, and the concentration of chloride ions increases along with that, so there is no regeneration. For that reason, when the pH of the site to be measured is a prescribed value or higher, when there are no chloride ions in the site to be measured, the self-potential of the first electrode in a high state (more noble state) is maintained with stability, but when chloride ions infiltrate the site to be measured, the first electrode gap corrosion advances, and the self-potential of the first electrode decreases (becomes less noble).

In view of such a fact, it is possible to detect with high sensitivity the fact that chloride ions have infiltrated the site to be measured based on the difference in electric potential of the first electrode and the second electrode.

In the sensor device according to the above described aspect of the present invention, the first metallic material and the second metallic material are preferably the same type of metallic material.

Thereby, in a state for which a passivation film is formed respectively on the first electrode and the second electrode, the difference in electric potential between the first electrode and the second electrode is in accordance with the chloride ion concentration of the site to be measured. For that reason, it is possible to detect with higher sensitivity the fact that chloride ions have infiltrated the site to be measured.

In the sensor device according to the above described aspect of the present invention, the first metallic material and the second metallic material are preferably different metallic materials.

Thereby, the formation or elimination timing of the first electrode passivation film can be made different from the formation or elimination timing of the second electrode passivation film. For that reason, it is possible to detect whether or not the pH of the site to be detected is a prescribed value or lower based on the difference in electric potential between the first electrode and the second electrode.

In the sensor device according to the above described aspect of the present invention, each of the first metallic material and the second metallic material is preferably iron or an iron-based alloy.

Iron or iron-based alloys (iron-based materials) are more readily and more inexpensively procured. In a case where, for example the sensor device is used to measure the state of a concrete structure, then at least one electrode of the first electrode and the second electrode can be composed of the same material (or material approximate to that) as the reinforcing bars inside the concrete structure, and it is possible to effectively detect the state of corrosion of the reinforcing bars inside the concrete structure.

In the sensor device according to the above described aspect of the present invention, a recess is preferably formed on the surface of the first electrode, and the gap forming member preferably covers the recess with the gap being formed between a wall surface of the recess and the gap forming member, and includes a through-hole or through-groove connecting to the recess.

Thereby, it is possible to easily and reliably form a gap for which first electrode gap corrosion can occur between the first electrode and the gap forming member.

In the sensor device according to the above described aspect of the present invention, each of the first electrode and the gap forming member preferably has a plate shape or a sheet shape, and the gap forming member is preferably fixed to the first electrode in a mutually overlapping state using a fixing member.

Thereby, it is possible to easily and reliably form a gap for which first electrode gap corrosion can occur between the first electrode and the gap forming member.

In the sensor device according to the above described aspect of the present invention, the gap forming member is preferably composed of a material with insulating properties.

Thereby, it is possible to prevent adverse effects by the gap forming member on the self-potential of the first electrode. For that reason, designing of the first electrode and the gap forming member is easy.

In the sensor device according to the above described aspect of the present invention, the gap forming member is preferably composed of the same type of metallic material as the first metallic material.

Thereby, it is possible to prevent adverse effects by the gap forming member on the self-potential of the first electrode. For that reason, designing of the first electrode and the gap forming member is easy.

In the sensor device according to the above described aspect of the present invention, the gap forming member preferably has alkaline resistant properties.

Thereby, even when the site to be measured is concrete, it is possible for the gap forming member to have excellent durability. For that reason, it is possible to measure the concrete state with stability over a long period.

In the sensor device according to the above described aspect of the present invention, a distance between the gap forming member and the first electrode at the gap is preferably 1 µm or greater and 100 µm or less.

Thereby, it is possible to have gap corrosion of the first electrode occur.

In the sensor device according to the above described aspect of the present invention, the functional element is preferably configured and arranged to detect whether or not a pH or a chloride ion concentration at the measurement site is at or below a prescribed value based on the difference in electric potential between the first electrode and the second electrode.

This makes it possible to detect the changes in state of an object to be measured which accompany changes in the pH or chloride ion concentration thereof.

The sensor device according to the above described aspect of the present invention preferably further includes an antenna, and a communication circuit configured and arranged to provide power to the antenna. The functional element is preferably further configured and arranged to drive and control the communication circuit.

This makes it possible to wirelessly transmit measurement results to the outside of the object to be measured.

BRIEF DESCRIPTION OF THE DRAWINGS

Referring now to the attached drawings which form a part of this original disclosure:

FIGS. 11A to 11C are partial plan views illustrating a modification example of the first electrode and the gap forming member illustrated in FIG. 2.

DETAILED DESCRIPTION OF EXEMPLARY EMBODIMENTS

The following is a description of preferred embodiments of the sensor device of the present invention, with reference to the accompanying drawings.

First Embodiment

The first embodiment of the present invention shall be described first.

Figure 1:
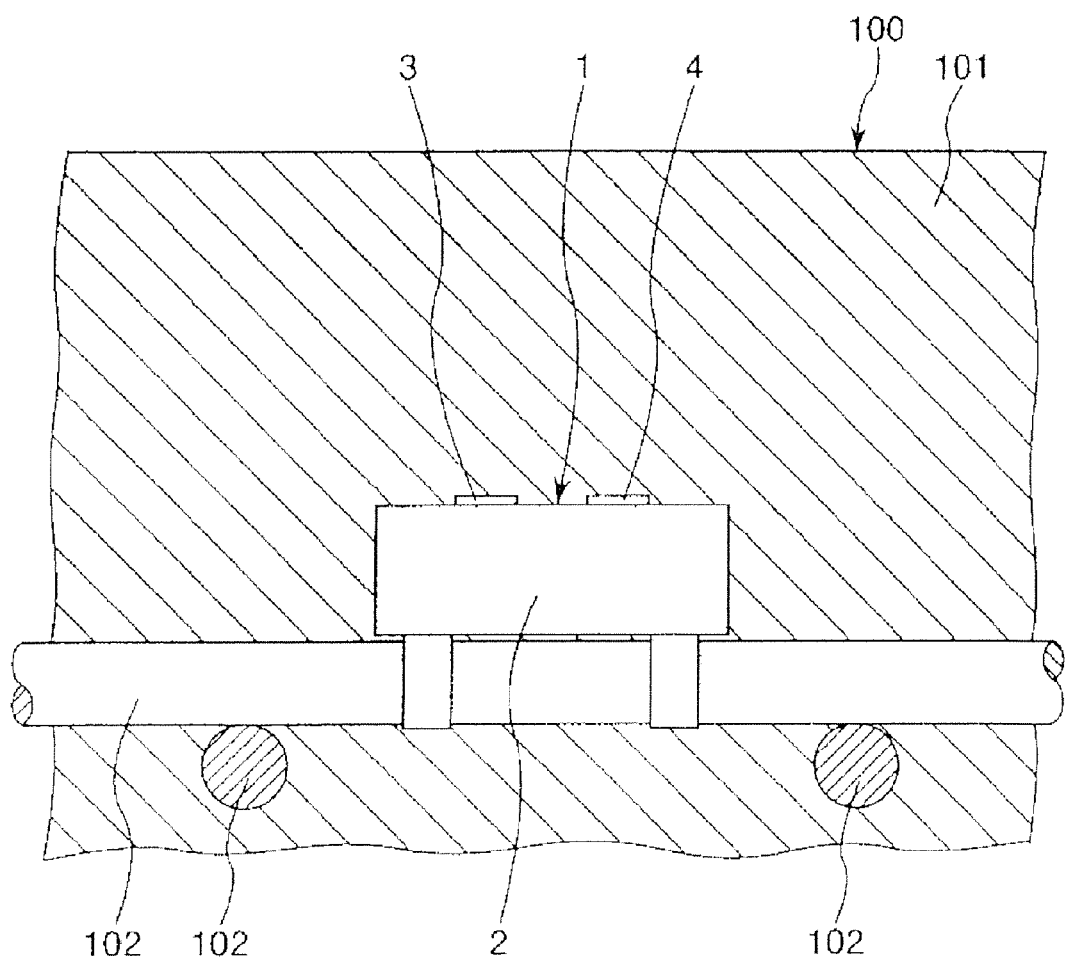
FIG. 1 is a drawing illustrating an example of the state of use of a sensor device according to a first embodiment of the present invention.
Figure 2:
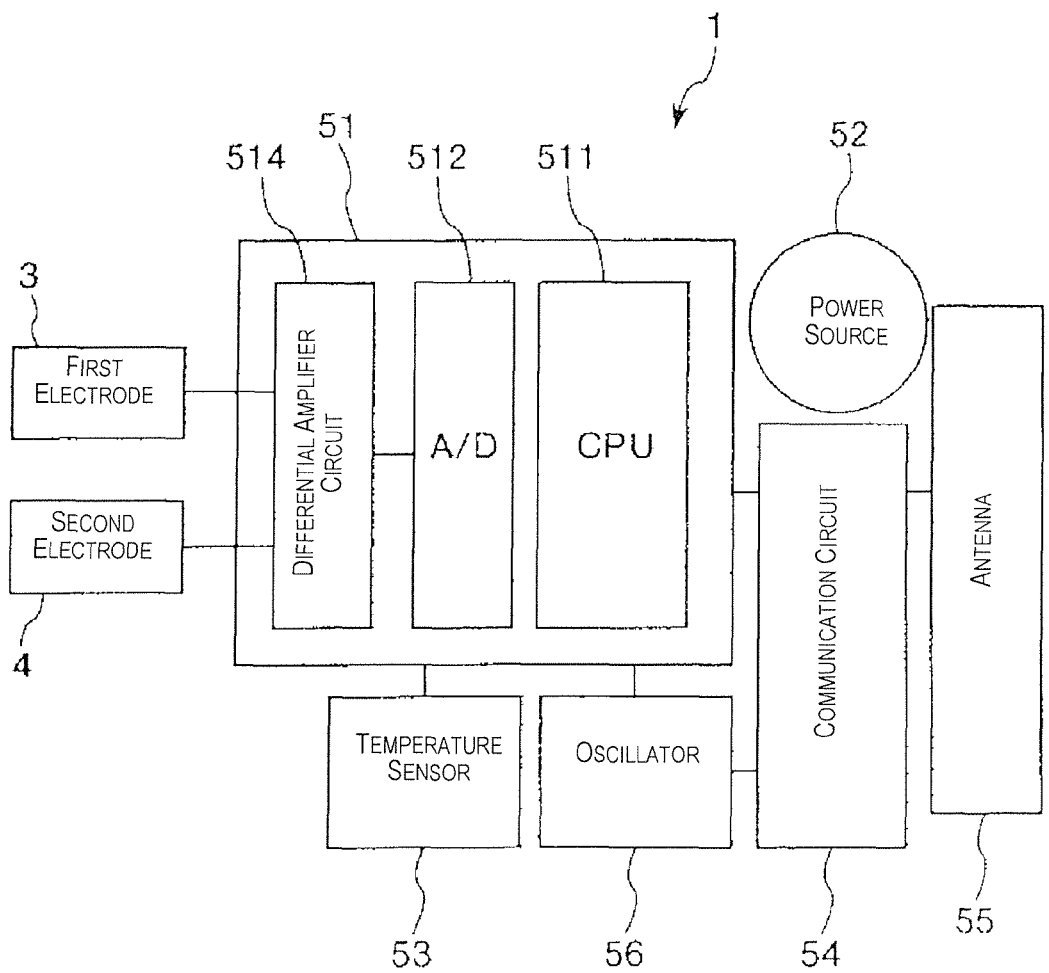
FIG. 2 is a block diagram illustrating a schematic configuration of the sensor device illustrated in FIG. 1.
Figure 3:
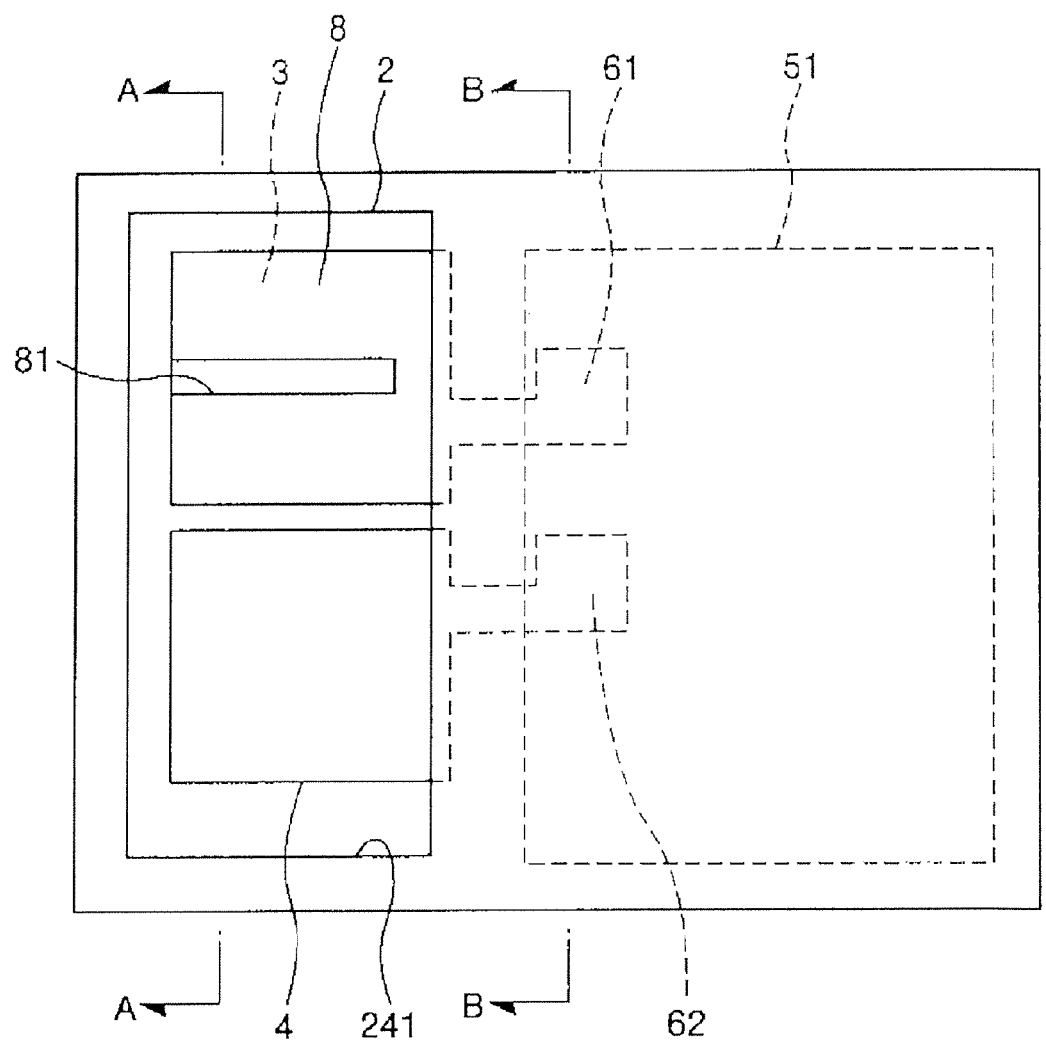
FIG. 3 is a plan view of a first electrode, a second electrode, a gap forming member, and a functional element illustrated in FIG. 2.
Figure 4:
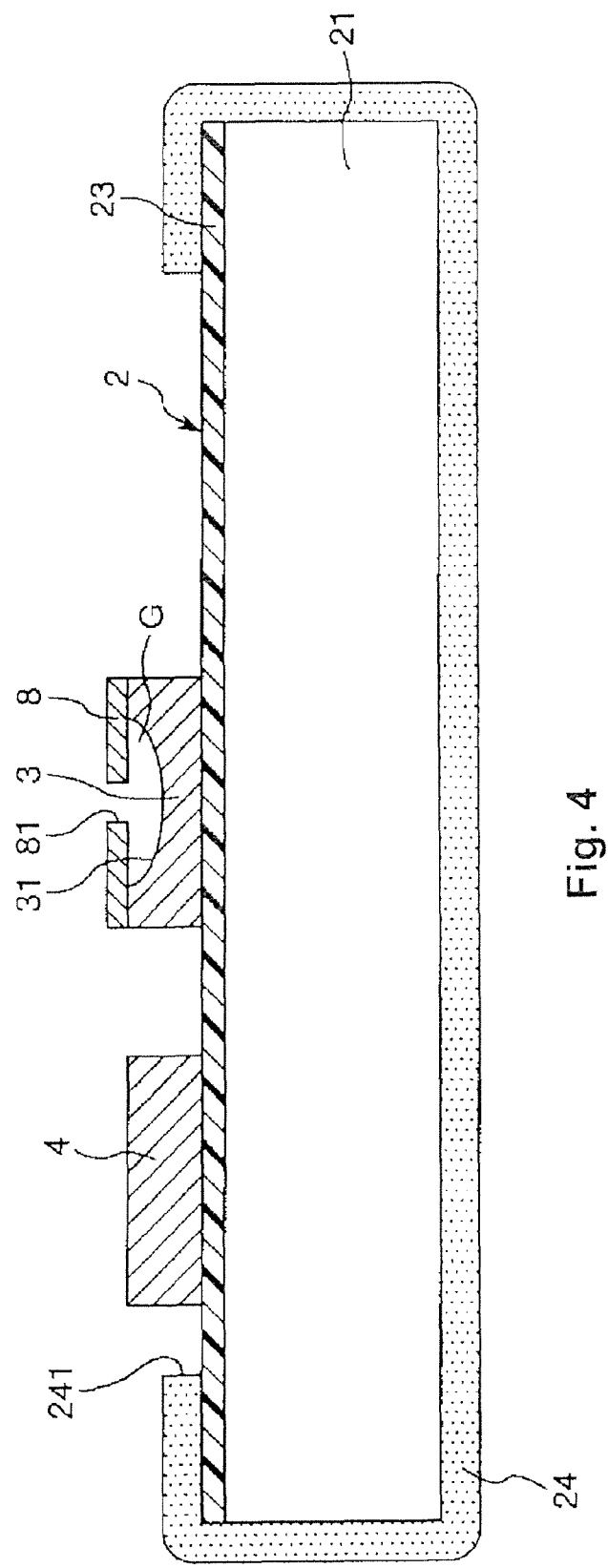
FIG. 4 is a cross-sectional view (a cross-sectional view along line A-A in FIG. 3) for describing the first electrode, the second electrode, and the gap forming member illustrated in FIG. 2.
Figure 5:
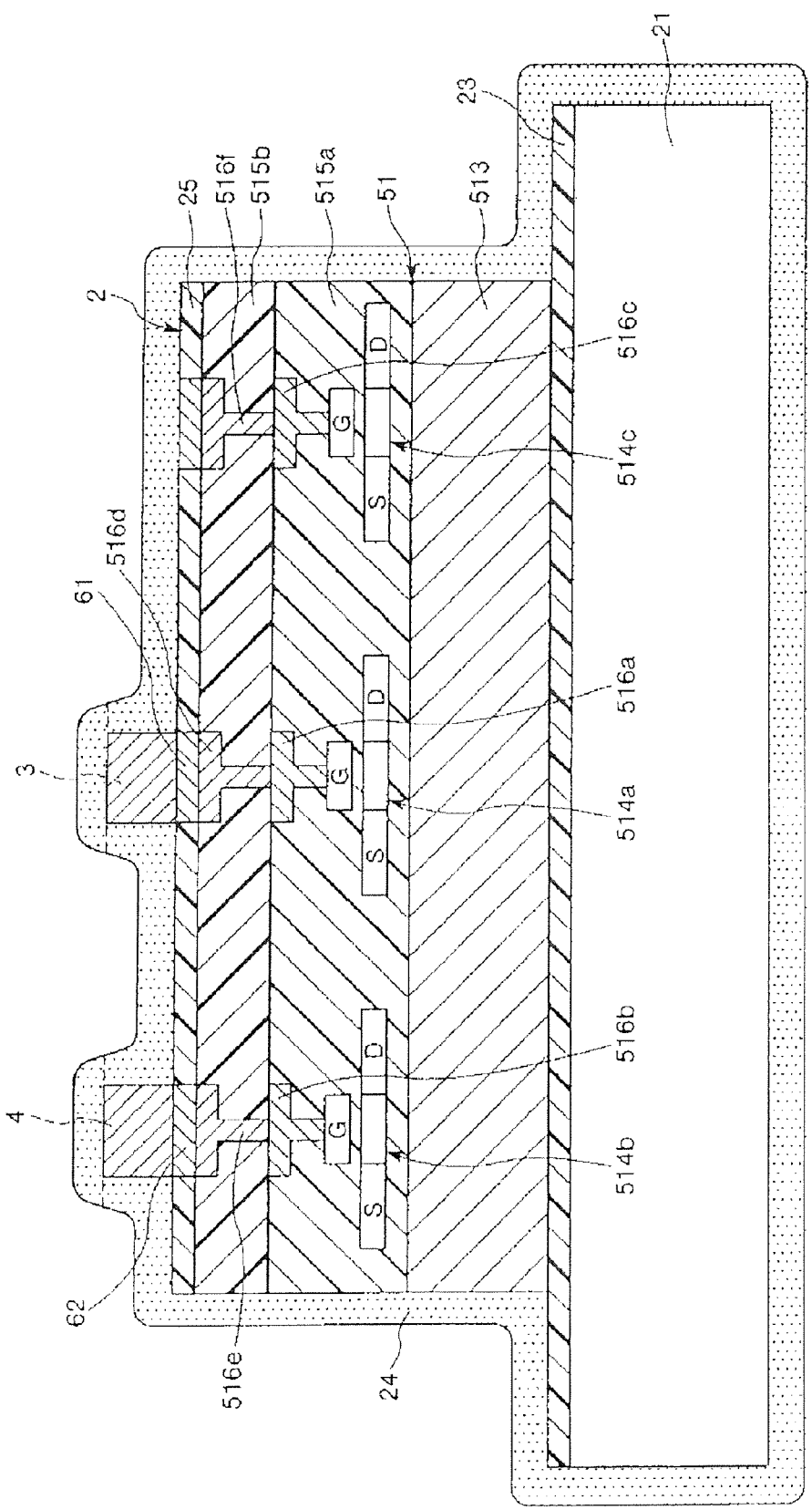
FIG. 5 is a cross-sectional view (a cross-sectional view along line B-B in FIG. 3) for describing the functional element illustrated in FIG. 2.
Figure 6:
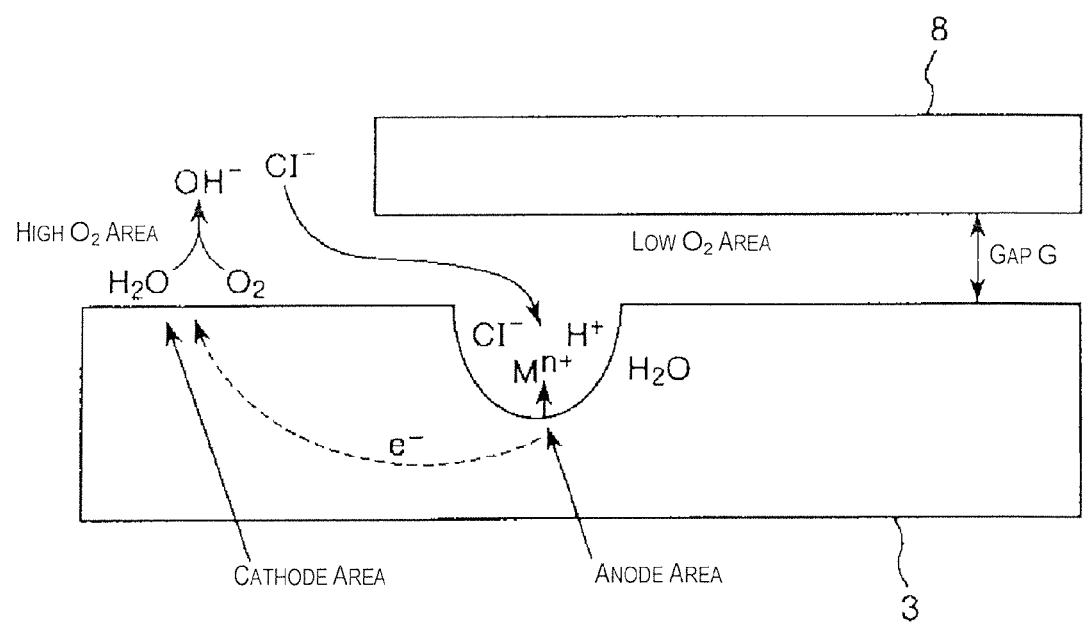
FIG. 6 is a schematic diagram for describing corrosion due to chloride ions of the first electrode illustrated in FIG. 2.
Figure 7:
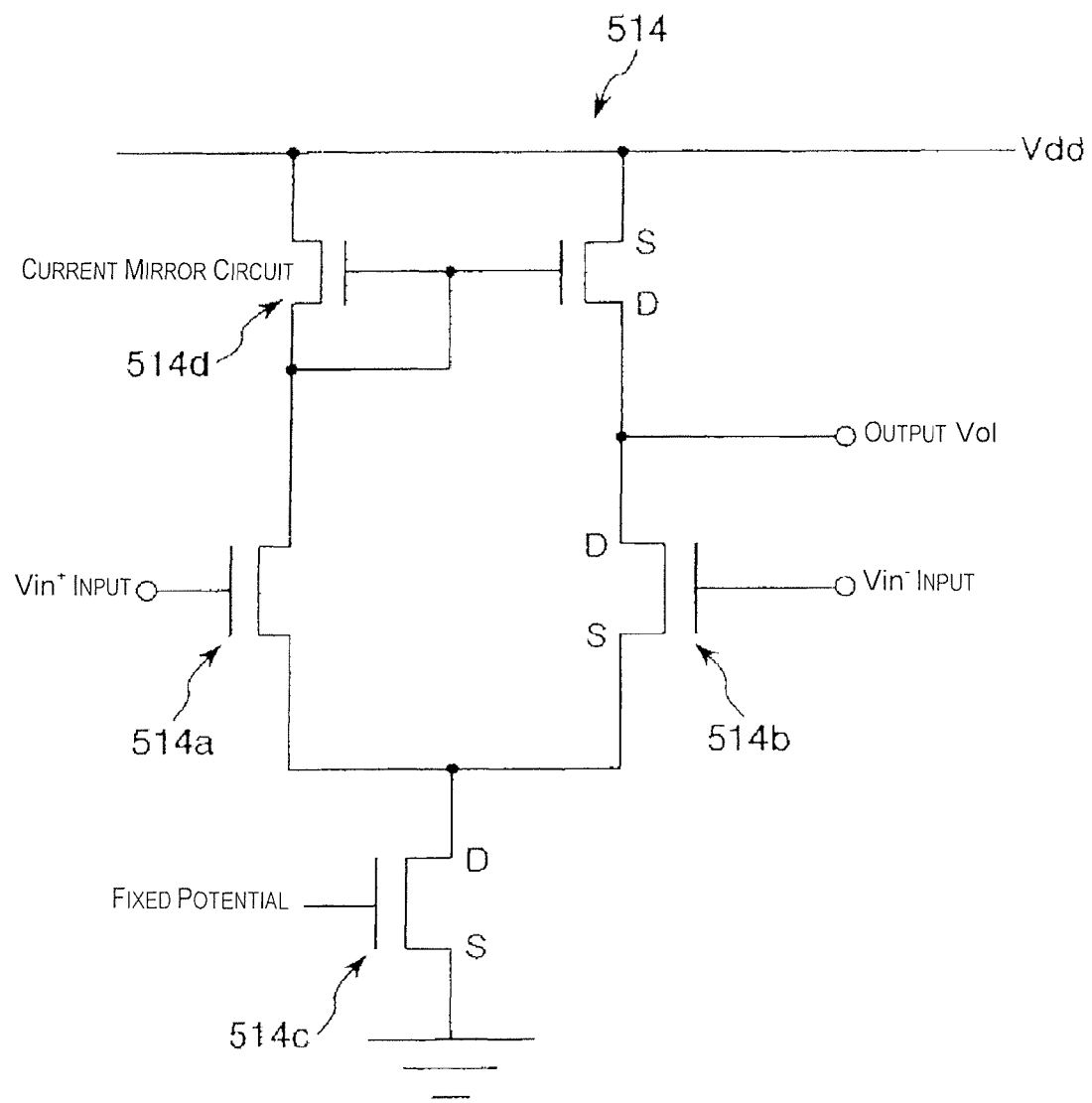
FIG. 7 is a circuit diagram illustrating a differential amplifier circuit provided to the functional element illustrated in FIG. 2.
Figure 8:
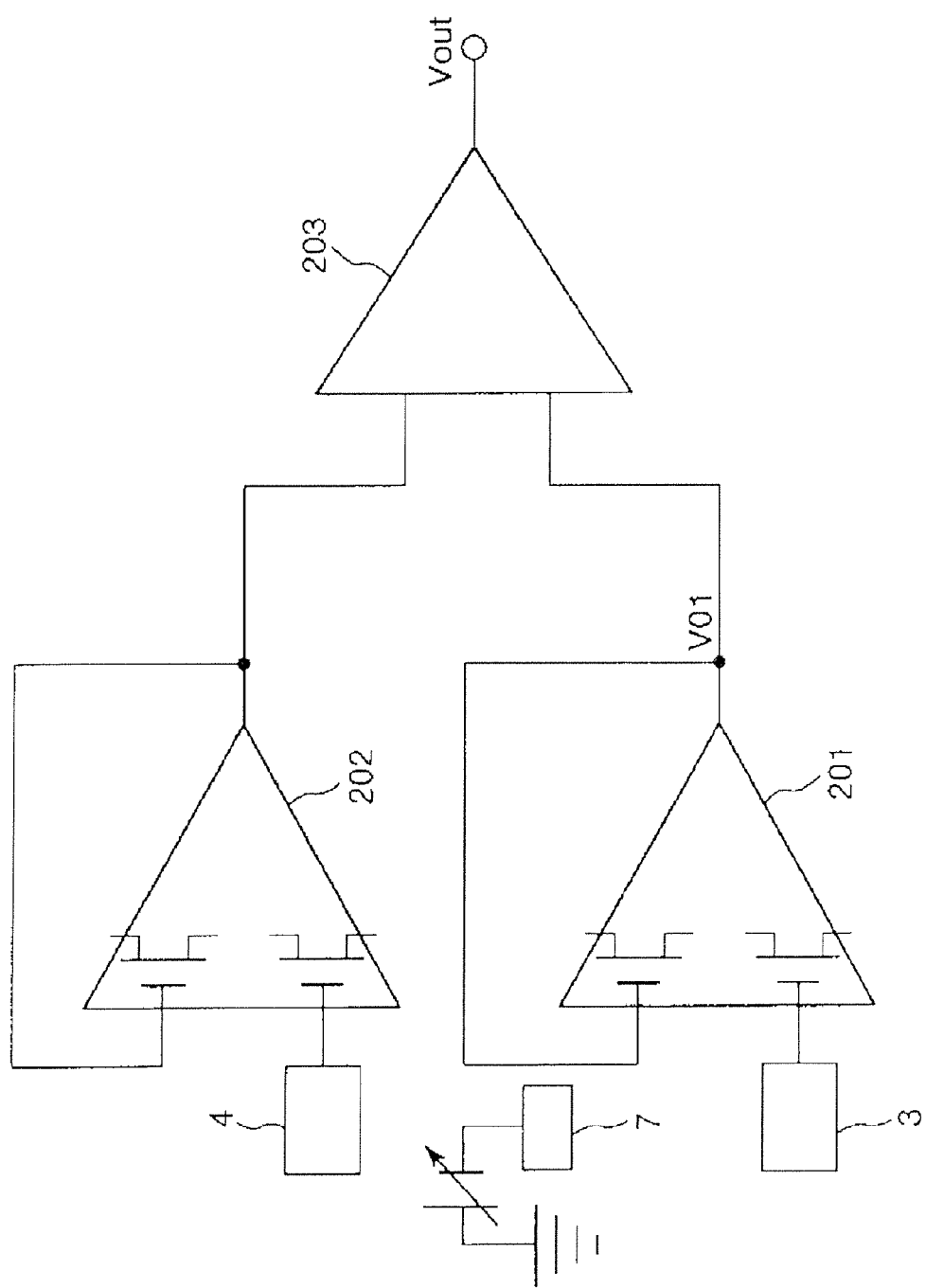
FIG. 8 is a circuit diagram illustrating the differential amplifier circuit provided to the functional element illustrated in FIG. 2.
Figure 9A:
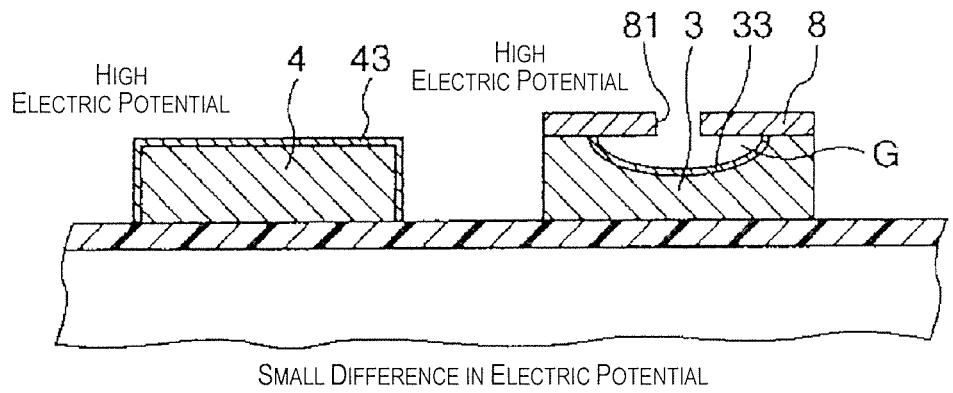
FIGS. 9A to 9C are drawings for describing an example of the action of the sensor device shown in FIG. 1.
Figure 9B:
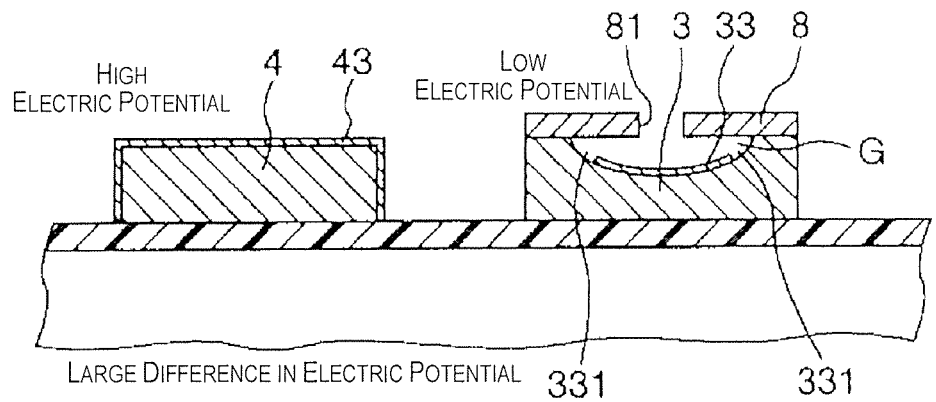
Figure 9C:
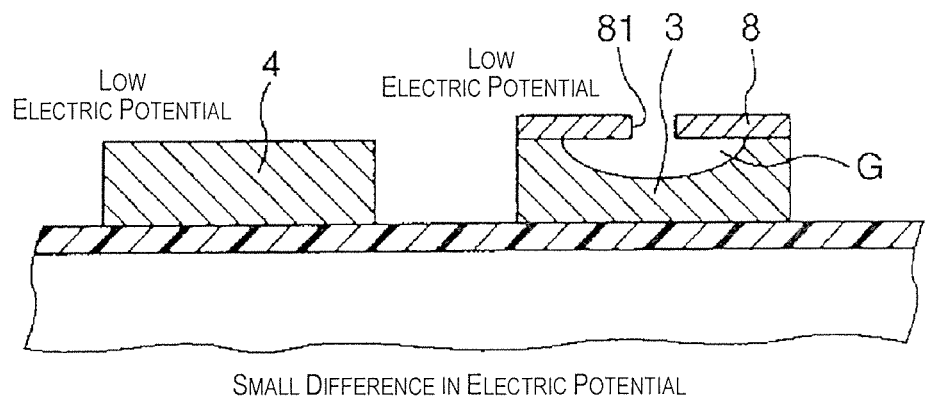
Figure 10A:
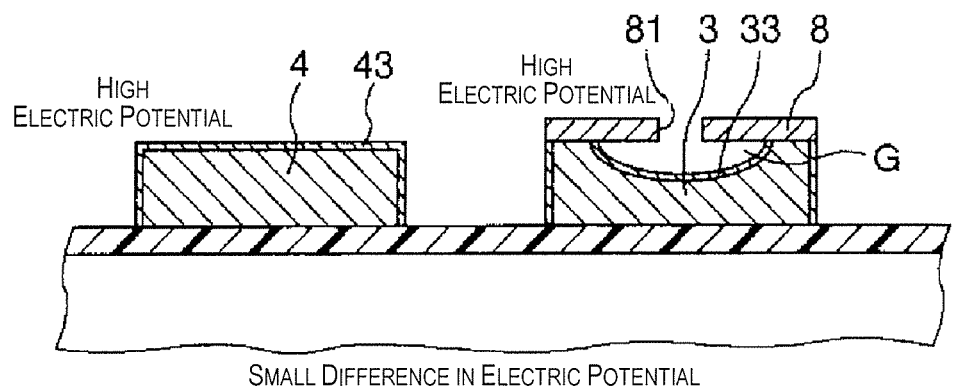
FIGS. 10A to 10C are drawings for describing another example of the action of the sensor device illustrated in FIG. 1.
Figure 10B:
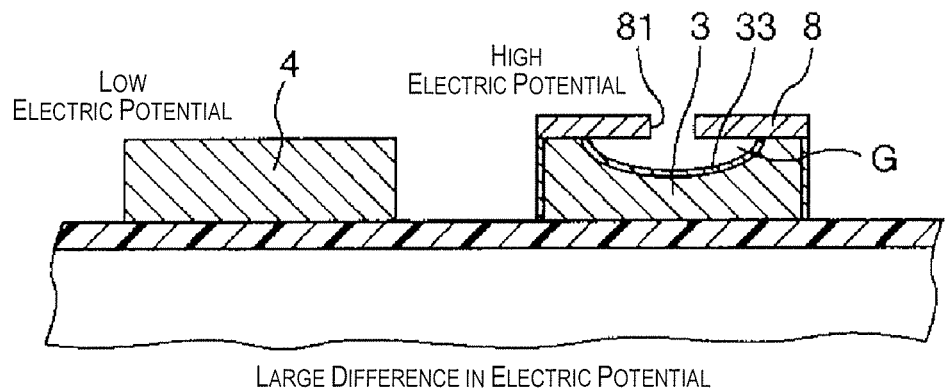
Figure 10C:
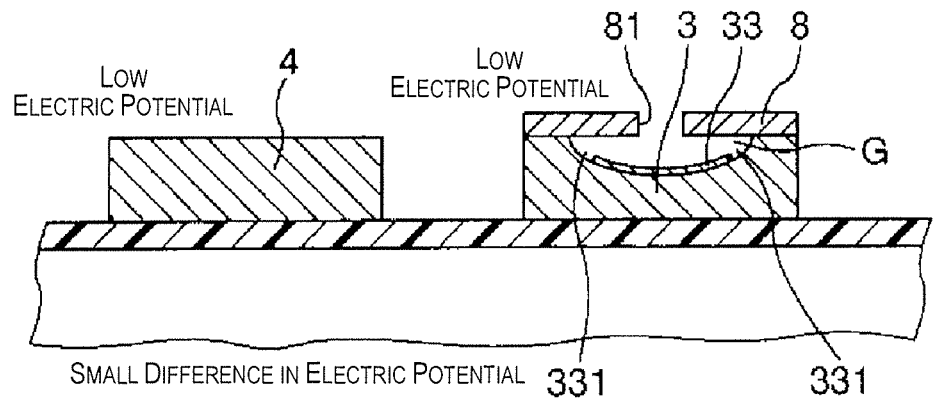

FIG. 1 is a drawing illustrating an example of the state of use of a sensor device according to a first embodiment of the present invention. FIG. 2 is a block diagram illustrating a schematic configuration of the sensor device illustrated in FIG. 1. FIG. 3 is a plan view of a first electrode, a second electrode, a gap forming member, and a functional element illustrated in FIG. 2. FIG. 4 is a cross-sectional view (a cross-sectional view along line A-A in FIG. 3) of the first electrode, the second electrode, and the gap forming member illustrated in FIG. 2. FIG. 5 is a cross-sectional view (a cross-sectional view along line B-B in FIG. 3) of the functional element illustrated in FIG. 2. FIG. 6 is a schematic diagram for describing corrosion due to chloride ions of the first electrode illustrated in FIG. 2. FIGS. 7 and 8 are each circuit diagrams illustrating a differential amplifier circuit provided to the functional element illustrated in FIG. 2. FIGS. 9A to 9C are drawings for describing an example of the action of the sensor device illustrated in FIG. 1. FIGS. 10A to 10C are drawings for describing another example of the action of the sensor device illustrated in FIG. 1. FIGS. 11A to 11C are partial plan views illustrating a modification example of the first electrode and the gap forming member illustrated in FIG. 2.

The example described below is that of a case where the sensor device of the present invention is used to measure the quality of a concrete structure.

A sensor device 1 shown in FIG. 1 is intended to measure the quality of a concrete structure 100.

The concrete structure 100 has a plurality of reinforcing bars 102 embedded in concrete 101. The sensor device 1 is also embedded within the concrete 101 of the concrete structure 100, in the vicinity of the reinforcing bars 102. Also, the sensor device 1 may be embedded when the concrete structure 100 is being cast, prior to the casting of the concrete 101, so as to be fixed to the reinforcing bars, or may be embedded in holes bored into the concrete 101 having hardened after casting.

The sensor device 1 has a main body 2, as well as a first electrode 3 and a second electrode 4 provided on the main body 2. Also though omitted for convenience of illustration in FIG. 1, the sensor device 1 has a gap forming member 8 provided on the first electrode 3 (see FIG. 3).

In the present embodiment, the first electrode 3 and the second electrode 4 are installed on the outer surface of the concrete structure 100 further out than the reinforcing bars 102 so that both are equidistant from the outer surface of the concrete structure 100. The first electrode 3 and the second electrode 4 are also installed such that the respective electrode surfaces thereof are parallel or substantially parallel to the outer surface of the concrete structure 100. The first electrode 3 and the second electrode 4 are also configured such that the difference in electric potential therebetween changes in association with changes in the state of a site to be measured of the concrete 101. More detailed descriptions of the first electrode 3 and the second electrode 4 shall be provided below.

The sensor device 1, as illustrated in FIG. 2, also has a functional element 51, a power source 52, a temperature sensor 53, a communication circuit 54, an antenna 55, and an oscillator 56, which are electrically connected to the first electrode 3 and to the second electrode 4 and are housed within the main body 2.

The following is a sequential description of each of the parts constituting the sensor device 1.

Main Body

The main body 2 has a function for supporting the first electrode 3, the second electrode 4, the functional element 51, and other elements.

Such a main body 2, as illustrated in FIG. 4 and FIG. 5, has a substrate 21 for supporting the first electrode 3, the second electrode 4, and the functional element 51. The substrate 21 is also intended to support the power source 52, the temperature sensor 53, the communication circuit 54, the antenna 55, and the oscillator 56, but FIGS. 3 to 5 omit a depiction of the power source 52, the temperature sensor 53, the communication circuit 54, the antenna 55, and the oscillator 56, for convenience of description.

The substrate 21 has insulating properties. Examples which can be used as the substrate 21 include, but are not particularly limited to, an alumina substrate, a resin substrate, or the like.

As shown in FIG. 4, an insulating layer 23 composed of an insulating resin composition, such as, for example, a solder resist, is provided on the substrate 21. The first electrode 3, the second electrode 4, and the functional element 51 are also mounted onto the substrate 21 via the insulating layer 23.

As illustrated in FIG. 5, the functional element 51 (an integrated circuit chip) is retained on the substrate 21, and conductor parts 61, 62 (an electrode pad) of the functional element 51 are connected to the first electrode 3 and the second electrode 4.

The conductor part 61 electrically connects the first electrode 3 with conductor parts 516a, 516d as well as with a gate electrode of a transistor 514a. The conductor part 62 electrically connects the second electrode 4 with conductor parts 516b, 516e as well as with a gate electrode of a transistor 514b. Each of the first electrode 3 and the second electrode 4 is in a floating state because of the respective connections thereof with the gate electrodes of the transistors 514a, 514b. Reference numerals 515a and 515b indicate interlayer insulating films of the integrated circuit, and reference numeral 25 indicates a protective film of the integrated circuit.

The main body 2 also has a function for housing the functional element 51, the power source 52, the temperature sensor 53, the communication circuit 54, the antenna 55, and the oscillator 56.

In particular, the main body 2 is configured so as to provide a liquid-tight housing for the functional element 51, the power source 52, the temperature sensor 53, the communication circuit 54, the antenna 55, and the oscillator 56.

Specifically, as illustrated in FIGS. 4 and 5, the main body 2 has a sealing part 24. The sealing part 24 has a function for sealing in the functional element 51, the power source 52, the temperature sensor 53, the communication circuit 54, the antenna 55, and the oscillator 56. This makes it possible to prevent the deterioration of the functional element 51, the power source 52, the temperature sensor 53, the communication circuit 54, the antenna 55, and the oscillator 56 in a case where the sensor device 1 is installed in the presence of moisture or concrete.

Herein, the sealing part 24 has an opening part 241, and is provided such that each of the parts other than the first electrode 3 and the second electrode 4 are covered, while the first electrode 3 and the second electrode 4 are exposed from the opening part 241 (see FIGS. 3 and 4). This makes it possible for the sensor device 1 to measure while the sealing part 24 prevents each of the parts other than the first electrode 3 and the second electrode 4 from deteriorating. The opening part 241 may also be formed such that at least a part or more of the first electrode 3 and at least a part or more of the second electrode 4 is exposed via a through-groove 81 or a gap G of the gap forming member 8.

Examples of materials which can be used to constitute the sealing part 24 include: a thermoplastic resin, such as an acrylic-based resin, a urethane-based resin, or an olefin-based resin; a thermosetting resin, such as an epoxy-based resin, a melamine-based resin, or a phenol-based resin; and various other types of resin materials, it being possible to use one type thereof or a combination of two or more types thereof.

The sealing part 24 may be provided or can be omitted, in accordance with need.

First Electrode and Second Electrode

The first electrode 3 and the second electrode 4, as illustrated in FIG. 4, are each provided on the outer surface of the main body 2 described above (more specifically, on the substrate 21). In particular, the first electrode 3 and the second electrode 4 are provided on the same plane. For this reason, it is possible to prevent the emergence of differences in the installation environments of the first electrode 3 and the second electrode 4.

The first electrode 3 and the second electrode 4 are spaced apart to such an extent (for example, several millimeters) that there is no mutual influence due to electric potential.

In the present embodiment, each of the first electrode 3 and the second electrode 4 forms a plate shape or a sheet shape. Each of the shapes in plan view of the first electrode 3 and the second electrode 4 also forms a quadrangle. The first electrode 3 and the second electrode 4 have mutually equivalent shapes and surface areas in plan view. It is also possible for the first electrode 3 and the second electrode 4 to have mutually different shapes and surface areas in plan view.

With this embodiment, a recess 31 is formed on the top surface of the first electrode 3 (specifically, the surface on the opposite side to the substrate 21). As a result, it is possible to form the gap G between the first electrode 3 and the gap forming member 8 in a state with the gap forming member 8 joined to the top surface of the first electrode 3 as will be described later.

The recess 31, for example, can be formed by etching using the gap forming member 8 as a mask (specifically wet etching) in a state with the gap forming member 8 joined to the first electrode 3 before formation of the recess 31. By forming the recess 31 in this way, it is possible to easily and reliably form a gap G for which corrosion of the first electrode 3 due to chloride ions such as that described later can be promoted between the first electrode 3 and the gap forming member 8. The forming method of the recess 31 is not restricted to this.

Also, the depth of the recess 31 (maximum depth) is not particularly restricted provided it is possible to form a gap G for which it is possible to promote the kind of corrosion of the first electrode 3 due to chloride ions described later, but for example, it is preferably 1 μm or greater and 100 μm or less, more preferably 10 μm or greater and 80 μm or less, and even more preferably 20 μm or greater and 60 μm or less. As a result, it is possible to easily and reliably form the gap G for which gap corrosion of the first electrode 3 described later can occur.

Also, the width of the recess 31 is not particularly restricted provided it is possible to form a gap G for which the kind of gap corrosion of the first electrode 3 described later can occur.

It is also preferable that the first electrode 3 be constituted with at least one surface vicinity being a compact body. As a result, with the first electrode 3, in the presence of chloride ions, the part for which corrosion occurs most easily is corroded first, and since the ease of corrosion of the part for which the first corrosion occurred becomes greater than that of the other parts, localized corrosion (pitting) occurs.

Also, with the second electrode 4, preferably, at least its surface vicinity is constituted with a porous body. As a result, as the part for which corrosion occurs easily, many fine recesses are formed dispersed evenly on the surface of the second electrode 4. For that reason, with the surface of the second electrode 4, in the presence of chloride ions, corrosion occurs evenly, and localized corrosion (pitting) is inhibited.

Also, when the second electrode 4 is constituted using a porous body as described above, the average diameter of the holes of the porous body is not particularly restricted provided it is in a range for which pitting due to chloride ions like that described above can be prevented, but for example, this is preferably 2 nm or greater and 50 nm or less. Specifically, the holes are preferably mesopores. Also, the porosity of the porous body is not particularly restricted provided it is within a range for which it is possible to prevent pitting due to chloride ions as described previously, but for example, this is preferably 10% or greater and 90% or less.

By constituting the second electrode 4 using a porous body having holes of an average diameter within this range, it is possible to prevent pitting of the second electrode 4 due to chloride ions such as that described previously, and also to cause moisture to condense on the second electrode at a lower relative humidity using the capillary condensation effect due to fine holes. For this reason, a stable presence of liquid water can be maintained on the second electrode 4. Specifically, even at a relatively low humidity for which condensation does not occur on the second electrode 4 in a case such as when the second electrode 4 is constituted with a compact body, it is possible to respectively condense and maintain liquid water on the second electrode 4.

In view of such a fact, a fluctuation in the amount of moisture on the second electrode 4 can be prevented even though the relative humidity inside the concrete 101 may change in association with changes in the humidity or temperature of the external environment. Consequently, changes in the humidity or temperature of the external environment can be prevented from causing the self-potential of the second electrode 4 to fluctuate, and the state of the site to be measured of the concrete 101 can be measured with a high degree of precision.

Here, we will describe the constituent materials of the first electrode 3 and the second electrode 4.

The first electrode 3 is composed of a first metallic material (which hereinafter is also simply called the "first metallic material") for forming a passivation film (a first passivation film). In the first electrode 3 having such a configuration, a passivation film is either formed or destroyed depending on changes in the pH. In the state where the passivation film has been so formed (the passivated state) on the first electrode 3, inactive (noble) conditions are in effect and self-potential increases (a shift towards increased nobility occurs). In the state where the passivation film has been destroyed (eliminated state), the first electrode 3 is active (of less nobility). For this reason, the electric potential of the first electrode 3 has sharp changes depending on the presence or absence of the passivation film, as associated with changes in pH.

The first metallic material is not particularly limited, provided that a passivation film is formed; examples thereof include iron, nickel, magnesium, zinc, an alloy containing these elements, or the like.

For example, iron forms a passivation film when the pH is greater than 9. Iron-aluminum-based carbon steel (0.8% Al) also forms a passivation film when the pH is greater than 4. Nickel forms a passivation film when the pH is 8 to 14. Magnesium forms a passivation film when the pH is greater than 10.5. Zinc forms a passivation film when the pH is 6 to 12. Also, SUS304 forms a passivation film when the pH is 2 to 13.

Also, for example, with carbon steel (SD345), destruction of the passivation film starts when the chloride ion concentration exceeds approximately 1.2 kg/m$^3$.

Of these, the first metallic material is preferably iron or an alloy containing iron (an iron-based alloy), i.e., an iron-based material (specifically, carbon steel, alloy steel, SUS, and the like). Iron-based materials are comparatively more readily and more inexpensively procured. In a case where, as in the present embodiment, the sensor device 1 is used to measure the state of the concrete structure 100, then the first metallic material can be a material identical to or approximating that of the reinforcing bars 102 of the concrete structure 100, and it is possible to effectively detect a state of a corrosive environment of the reinforcing bars 102. In the case where, for example, the first electrode 3 is composed of iron, then a determination can be made as to whether or not the pH is 9 or greater.

On the other hand, the second electrode 4 is composed of a second metallic material (which hereinafter is also simply called "the second metallic material").

Various types of metallic materials can be used as the second metallic material without particular limitation, provided that it is a metallic material which allows the second electrode 4 to function as an electrode.

The second metallic material may be the same material as the aforesaid first metallic material (the same or one that approximates it), or may be a material that is different from the aforesaid first metallic material.

Also, the second metallic material may form a passivation film or may not form a passivation film.

When the first metallic material and the second metallic material are the same type of material, with the first electrode 3 and the second electrode 4, the same or approximately the same state mutually changes in relation to pH changes of the site to be measured. Therefore, even when the pH of the site to be measured changes, the difference in electric potential of the first electrode 3 and the second electrode 4 changes not at all or almost doesn't change. For that reason, it is possible distinguish between the change in chloride ion concentration of the site to be measured and the change in pH of the site to be measured and perform measurement.

Specifically, in a state with a passivation film faulted on both the surface of the first electrode 3 and the second electrode 4, the difference in electric potential of the first electrode 3 and the second electrode 4 is in accordance with the chloride ion concentration of the site to be measured. For that reason, it is possible to detect with a higher sensitivity the fact that chloride ions have infiltrated the site to be measured based on the difference in electric potential of the first electrode 3 and the second electrode 4.

On the other hand, when the first metallic material and the second metallic material are mutually different, when the second metallic material forms a passivation film (second passivation film), it is possible to make the timing of the formation or elimination of the first electrode 3 passivation film different from the timing of the formation or elimination of the second electrode 4 passivation film. For that reason, it is possible to detect whether or not the pH of the site to be measured is a prescribed value or less based on the difference in electric potential of the first electrode and the second electrode.

For example, as the pH of the site to be measured decreases, when the timing at which the passivation film of the first electrode 3 is eliminated is earlier than the timing at which the passivation film of the second electrode 4 is eliminated, with the second electrode 4, when the electric potential for the first electrode 3 changes according to whether or not there is a passivation film as described previously, there is no formation or destruction (elimination) of the passivation film, and there is no sharp change in the electric potential. For that reason, when the electric potential of the first electrode 3 changes according to whether or not there is a passivation film as described previously, there is a sharp change in the difference in electric potential between the first electrode 3 and the second electrode 4. For that reason, it is possible to accurately detect whether the pH of the first electrode 3 and the second electrode 4 installation environment (with this embodiment, near the reinforcing bars 102 of the concrete 101) is of a prescribed value or less.

Also, when the second metallic material forms a passivation film (second passivation film), the metals listed above as examples for the first metallic material can be used as the second metallic material.

When the first metallic material and the second metallic material are both metallic materials that form a passivation film, when the lower limit value of the pH range at which the first metallic material forms a passivation film is used as the first pH (first passivation pH), and the lower limit value of the pH range at which the second metallic material forms a passivation film is used as the second pH (second passivation pH), it is preferable that the first pH and the second pH be mutually different. Specifically, it is preferable that the first metallic material forms the passivation film when the pH becomes greater than the first pH, and that the second metallic material form a passivation film when the pH becomes greater than the second pH which is different from the first pH. As a result, it is possible to accurately detect whether pH of the environment in which the first electrode 3 and the second electrode 4 are respectively installed are the first pH or less and the second pH or less.

In such a case, preferably, the first pH is 8 or greater and 10 or lower, and the second pH is 7 or lower. This also makes it possible, by detecting whether or not [the pH is] at or lower than the first pH, to know in advance that the installation environments of the first electrode 3 and the second electrode 4 are approaching a neutral state. In view of such facts, in a case where the sensor device 1 is used to measure the state of the concrete structure 100, as in this embodiment, it is possible to act in advance to counter and prevent the corrosion of the reinforcing bars 102. It is also possible, by detecting whether or not [the pH is] at or lower than the second pH, to know that the installation environments of the first electrode 3 and the second electrode 4 (site to be measured) have reached an acidic state.

In such a case, preferably, the second metallic material is iron or an alloy containing iron (an iron-based alloy), i.e., an iron-based material. Iron-based materials are comparatively more readily and more inexpensively procured. Further, in a case where the sensor device 1 is used to measure the state of the concrete structure 100, as in this embodiment, then it is possible for the first metallic material to be the same material as the reinforcing bars 102. Having the second metallic material be the same material as the reinforcing bars 102 makes it possible to effectively detect the state of corrosion of the reinforcing bars 102.

On the other hand, in a case where the second metallic material does not form a passivation film, then possible examples of the second metallic material include platinum, gold, and the like. In a case where the second metallic material does not form a passivation film, then it is possible to know in a single stage, with a high degree of precision, the change when the installation environments of the first electrode 3 and the second electrode 4 change from a strongly alkaline state to a strongly acidic state.

In such a case, preferably, the first metallic material forms a passivation film when the pH thereof becomes greater than a pH of 3 to 5, or, greater than a pH of 8 to 10. It is possible, by detecting whether or not [the pH is] a pH of at or lower than a pH of 3 to 5, to know that the installation environments of the first electrode 3 and the second electrode 4 have reached an acidic state. Detecting whether or not [the pH] is at or below a pH of 8 to 10 also makes it possible to know in advance that the installation environments of the first electrode 3 and the second electrode 4 are approaching a neutral state.

As the forming method for this kind of first electrode 3 and second electrode 4, these are not particularly restricted, and known film forming methods may be used.

Gap Forming Member

The gap forming member 8 is arranged forming a gap G with a portion of the surface of the first electrode 3. This gap G is locally formed on the surface of the first electrode 3, and is connected to the outside via a through-groove 81 of the gap forming member 8 described later.

By forming this kind of gap G, even in a state for which the chloride ion concentration of the site to be measured is relatively low and corrosion of the second electrode 4 does not occur, it is possible to have corrosion of the first electrode 3 performed using gap corrosion. For that reason, even in a state for which the chloride ion concentration of the site to be measured is low, a difference in electric potential occurs between the first electrode 3 and the second electrode 4, and it is possible to detect the infiltration of chloride ions based on this difference in electric potential.

In particular, when the first electrode 3 and the second electrode 4 are respectively composed of metallic materials which form passivation films like those described above, the passivation film formed by the second electrode 4 is not destroyed until the chloride ion concentration of the site to be measured becomes relatively high, and even if local destruction occurs temporarily, regeneration occurs in an environment for which the pH is a prescribed value or greater. For that reason, when the pH of the site to be measured is a prescribed value or greater, during the time until the chloride ion concentration of the site to be measured becomes relatively high, the self-potential of the second electrode 4 is maintained with stability in a high state (more noble state).

On the other hand, with the passivation film formed by the first electrode 3, even when the chloride ion concentration of the site to be measured is relatively low, when localized destruction occurs temporarily due to chloride ions infiltrating the gap G between the first electrode 3 and the gap forming member G, within that gap G, the metal ion concentration eluted from the first electrode 3 increased, and in accordance with that, the chloride ion concentration increases, so there is no regeneration. For that reason, when the pH of the site to be measured is a set pH or greater, when there are no chloride ions at the site to be measured, the self-potential of the first electrode 3 is maintained with stability at a high state (more noble state), but when chloride ions infiltrate the site to be measured, the gap corrosion of the first electrode 3 progresses, and the self-potential of the first electrode 3 decreases (becomes less noble).

From such facts, it is possible to detect with high sensitivity the fact that chloride ions have infiltrated the site to be measured based on the difference in electric potential between the first electrode 3 and the second electrode 4.

Following, using FIG. 6, we will give a more detailed description regarding corrosion due to chloride ions (gap corrosion) of the first electrode 3 for which the gap G was formed with the gap forming member 8.

When the first electrode 3 is in the presence of chloride ions (Cl$^-$), when localized destruction of the passivation film formed on the surface of the first electrode 3 occurs temporarily due to chloride ions infiltrating inside the gap G, the first metallic material constituting the first electrode 3 is eluted into the gap G as a metal ion (Mn$^{n+}$).

For example, when the first metallic material is pure iron (Fe), using the reaction of

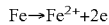

$$Fe \rightarrow Fe^{2+}+2e$$

The metal ions within the gap G are eluted as Fe$^{2+}$.

In this way, the metal ions eluted within the gap G have a slow diffusion speed, and are retained within the gap G. Because of this, the concentration of metal ions within the gap G increases.

As a result, so as to keep electrical neutrality within the gap G, the chloride ions migrate from outside the gap G to inside the gap G, and the chloride ions concentrate within the gap G. As a result, the concentration of the chloride ions within the gap G also increases.

For that reason, compared to the concentration of chloride ions outside the gap G, the concentration of chloride ions inside the gap G is higher.

Also, within the gap G, due to a reaction of the metal ions, chloride ions, and water, hydrogen ions are generated, and there is an increase in hydrogen ion concentration within the gap G, in other words, the pH within the gap G decreases.

For example, when the first metal material is pure iron (Fe), through the reactions of:

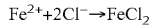

$$Fe^{2+}+2Cl^- \rightarrow FeCl_2$$

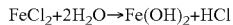

$$FeCl_2+2H_2O \rightarrow Fe(OH)_2+HCl$$

The concentration of hydrogen ions in the gap G increases.

For that reason, compared to the concentration of hydrogen ions outside the gap G, the concentration of hydrogen ions inside the gap G is higher.

From the kind of facts described above, even when the concentration of chloride ions and hydrogen ions outside the gap G is relatively low, the concentration of chloride ions and hydrogen ions inside the gap G increases, and the gap corrosion of the first electrode 3 progresses.

Here, with the surface of the first electrode 3, the part for which gap corrosion occurs is the anode area, and the part exposed to outside the gap G is the cathode area.

For example, when the first metallic material is pure iron (Fe), in the first electrode 3 anode area, an anode reaction of Fe→Fe$^{2+}$+2e occurs, and in the first electrode 3 cathode area, a cathode reaction of ½O$_2$+H$_2$O+2e→2OH— occurs.

With this kind of cathode reaction, by making the cathode area of the first electrode 3 bigger, the anode reaction is promoted. For that reason, by making the surface area of the apart exposed to outside the gap G of the surface of the first electrode 3, even in a state when the chloride ion concentration of the site to be measured is low, gap corrosion of the first electrode 3 occurs, so it is possible to detect with higher sensitivity the infiltration of chloride ions to the site to be measured.

The gap forming member 8 is provided covering the recess 31 while forming a gap with the wall surface of the recess 31 formed on the surface of the first electrode 3 described previously. With this embodiment, the gap forming member 8 forms a plate shape or sheet shape, and is joined to the opening edge part of the recess 31. A through-groove 81 that pierces through in the thickness direction is formed on the gap forming member 8. This through-groove 81 connects to the recess 31.

By combining a gap forming member 8 having this kind of through-groove 81 and the first electrode 3 having the recess 31, it is possible to easily and reliably form the gap G for which gap corrosion of the first electrode 3 can occur between the first electrode 3 and the gap forming member 8.

The through-groove 81 forms a long shape extending in one direction with a plan view. Note that the plan view shape of the through-groove 81 (through-hole) is not limited to this provided it is possible to form a gap G for which gap corrosion of the first electrode 3 can occur. A modification example of the through-groove 81 of the gap forming member 8 will be described in detail later.

The width of this through-groove 81 is not particularly restricted provided it is possible for there to be infiltration of chloride ions into the gap G as described above, and it is possible to form a gap G for which gap corrosion of the first electrode 3 can occur between the gap forming member 8 and the first electrode 3.

As the materials constituting this kind of gap forming member 8, this is not particularly restricted, but for example it is preferable to use the same type of metallic material as that of the first metallic material constituting the first electrode 3, and in particular, with this embodiment, from the perspective of being able to form the recess 31 of the first electrode 3 by etching using the gap forming member 8 as a mask as described previously, it is preferable to use materials with insulating properties.

When the gap forming member 8 is composed of a material with insulating properties, it is possible to prevent an adverse effect on the self-potential of the first electrode 3 by the gap forming member 8. For that reason, designing of the first electrode 3 and the gap forming member 8 becomes easy.

As such a material with insulating properties, though not particularly restricted, examples include insulating ceramic materials such as $SiO_2$, $Si_3N_4$ or the like, resin materials such as PSF (polysulfone), PAI (pre amide imide), PTFE (polytetrafluoroethylene), PVDF (polyvinylidene fluoride) and the like, and among these, with this embodiment, from the perspective of being able to form the recess 31 of the first electrode 3 by etching using the gap forming member 8 as a mask as described previously, it is preferable to use an insulating ceramic material.

Also, when the gap forming member 8 is composed of the same metallic material as the metallic material constituting the first electrode 3, it is possible to prevent the gap forming member from adversely affecting the self-potential of the first electrode 3. For that reason, designing of the first electrode 3 and the gap forming member 8 is easy.

Also, the gap forming member 8 preferably has resistance to alkalinity. As a result, even when the site to be measured is concrete, it is possible for the gap forming member 8 to have excellent durability. For that reason, it is possible to measure the state of the concrete over a long period with stability.

Also, the distance between the gap forming member 8 and the first electrode 3 with the gap G (distance in the thickness direction of the first electrode 3) is preferably 1 μm or greater and 100 μm or less, more preferably 10 μm or greater and 80 μm or less, and even more preferably 20 μm or greater and 60 μm or less. As a result, it is possible to have gap corrosion of the first electrode 3 occur.

Functional Element

The functional element 51 is embedded in the interior of the previously described main body 2. The surface of the substrate 21 of the main body 2 to which the functional element 51 is provided may be identical to or opposite from that of the first electrode 3 and the second electrode 4.

The functional element 51 has a function for measuring the difference in electric potential between the first electrode 3 and the second electrode 4. This makes it possible to detect whether or not the chloride ion concentration of the installation environments of the first electrode 3 and the second electrode 4 are at or below a prescribed value, based on the difference in electric potential between the first electrode 3 and the second electrode 4.

The functional element 51 also has a function for detecting whether or not the pH or chloride ion concentration of the site to be measured of the concrete structure 100, which is the object to be measured, is at or below a prescribed value, based on the difference in electric potential between the first electrode 3 and the second electrode 4. This makes it possible to detect a change in state of the concrete structure 100 in association with a change in the pH or a change in the chloride ion concentration thereof.

Such a functional element 51 is, for example, an integrated circuit. More specifically, the functional element 51 is, for example, an MCU (a micro control unit) and has, as illustrated in FIG. 2, a CPU 511, an A/D conversion circuit 512, and a differential amplifier circuit 514.

A more specific description shall now be provided. The functional element 51, as illustrated in FIG. 5, has: a substrate 513; a plurality of transistors 514a, 514b, 514c provided on the substrate 513; interlayer insulating films 515a, 515b for covering the transistors 514a, 514b, 514c; conductor parts 516a, 516b, 516c, 516d, 516e, 516f constituting a wiring and a conductor post; a protective film 25; and conductor parts 61, 62 constituting an electrode pad.

The substrate 513 is, for example, an SOI substrate, on which the CPU 511 and the A/D conversion circuit 512 are formed. Using an SOI substrate as the substrate 513 makes it possible to make the transistors 514a to 514c into an SOI-type MOSFET.

The plurality of transistors 514a, 514b, 514c are each, for example, field-effect transistors (FbTs), and constitute a part of the differential amplifier circuit 514.

The differential amplifier circuit 514, as illustrated in FIG. 7, is constituted of the three transistors 514a to 514c as well as a current mirror circuit 514d.

The differential amplifier circuit 514 also has operating amplifiers 201, 202 and an operating amplifier 203, as illustrated in FIG. 8.

The operating amplifier 201 detects the electric potential of the first electrode 3 using a comparative electrode 7 as a reference. The operating amplifier 202 detects the electric potential of the second electrode 4 using the comparative electrode 7 as a reference. The operating amplifier 203 detects the difference between the outputted electric potential of the operating amplifier 201 and the outputted electric potential of the operating amplifier 202.

The conductor part 516a has one end connected to a gate electrode of the transistor 514a, and another end connected to the aforesaid conductor part 516d. The conductor part 516d is electrically connected to the first electrode 3 via the conductor part 61. An electrical connection is thereby formed between the first electrode 3 and the gate electrode of the transistor 514a. For this reason, the drain current of the transistor 514a changes in accordance with changes in the electric potential of the first electrode 3.

Similarly, the conductor part 516b has one end connected to a gate electrode of the transistor 514b, and another end connected to the aforesaid conductor part 516e. The conductor part 516e is electrically connected to the second electrode 4 via the conductor part 62. An electrical connection is thereby formed between the second electrode 4 and the gate electrode of the transistor 514b. For this reason, the drain current of the transistor 514b changes in accordance with changes in the electric potential of the second electrode 4.

The conductor part 516c has one end connected to a gate electrode of the transistor 514c, and another end connected to the aforesaid conductor part 516f, thus constituting a part of a circuit.

The functional element 51 is operated by energization from the power source 52. Provided that the power source 52 can supply electric power capable of operating the functional element 51, there is no particular limitation, and the power source 52 may be, for example, a battery such as a button-type battery, or may be a power source using an element having a power generation function, such as a piezoelectric element.

The functional element 51 is configured so as to be able to acquire detected temperature information on the temperature sensor 53. This makes it possible also to obtain information relating to the temperature of the site to be measured. The use of such information relating to the temperature makes it possible to more accurately measure the state of the site to be measured, or to anticipate changes in the site to be measured with a high degree of precision.

The temperature sensor 53 has a function for detecting the temperature of the site to be measured of the concrete structure 100, which is the object to be measured. Examples of temperature sensors which can be used as such a temperature sensor 53 include but are not particularly limited to a thermistor, a thermocouple or other various known types.

The functional element 51 also has a function for driving and controlling the communication circuit 54. For example, the functional element 51 respectively inputs, into the communication circuit 54, information relating to the difference in electric potential between the first electrode 3 and the second electrode 4 (which hereinafter is also simply called "electric potential difference information") as well as information relating to whether or not the pH or chloride ion concentration of the site to be measured is at or below a prescribed value (which hereinafter is also simply called "pH information"). The functional element 51 also additionally inputs, into the communication circuit 54, information relating to the temperature detected by the temperature sensor 53 (which hereinafter is also simply called "temperature information").

The communication circuit 54 has a function for supplying power to the antenna 55 (a transmitting function). This makes it possible for the communication circuit 54 to do wireless transmission of inputted information using an RF band or LF band (preferably the LF band) via the antenna 55. The transmitted information is received by a receiver (reader) provided outside the concrete structure 100.

The communication circuit 54 has, for example, a transmission circuit for transmitting electromagnetic waves, a modulation circuit having a function for modulating a signal, and the like. The communication circuit 54 may also have a down converter circuit having a function for converting a signal to a lower frequency, an up converter having a function for converting a signal to a higher frequency, an amplifier circuit having a function for amplifying a signal, a receiving circuit for receiving electromagnetic waves, a demodulating circuit having a function for demodulating a signal, and the like.

The antenna 55 is composed of, for example, a metallic material, carbon, or the like, but is not particularly limited thereto, and forms a winding wire, a thin film, or another form.

The functional element 51 is configured so as to be able to acquire a clock signal from the oscillator 56. This makes it possible to synchronize each of the circuits, or to add time information to each of the various forms of information.

The oscillator 56 is constituted of, for example, an oscillation circuit employing a crystal oscillator, but is not particularly limited thereto.

In a measurement method using the sensor device 1 configured as has been described above, the first electrode 3 and the second electrode 4 are each embedded in the concrete structure 100, which is the object to be measured, and the state of the concrete structure 100 is measured based on the difference in electric potential between the first electrode 3 and the second electrode 4.

Following, we will describe the operation of the sensor device 1 using as examples a case when the first electrode 3 and the second electrode 4 are respectively composed of carbon steel (SD345) (first example), and a case when the first electrode 3 is composed of SUS304, and the second electrode 3 is composed of carbon steel (SD345) (second example).

First Example

First, we will describe the action of the sensor device 1 when the first electrode 3 and the second electrode 4 are each composed of carbon steel (SD345).

In the concrete structure 100 immediately after casting, ordinarily, the concrete 101 exhibits a strong alkalinity when casting has been done appropriately. For this reason, at such a time, the first electrode 3 and the second electrode 4 each form stable passivation films. That is, as illustrated in FIG. 9A, a passivation film 33 is formed on the surface of the first electrode 3, and a passivation film 43 is formed on the surface of the second electrode 4. The self-potentials of the first electrode 3 and the second electrode 4 are thereby each made to increase (become more noble). As a result, the difference in electric potential between the first electrode 3 and the second electrode 4 immediately after the concrete has been cast is reduced.

Thereafter, in a state with the passivation films 33 and 43 formed, when chloride ions infiltrate the site to be measured of the concrete 101 of the concrete structure 100, during the time until that chloride ion concentration reaches the boundary concentration at which carbon steel is corroded, the passivation film 43 formed on the second electrode 4 maintains a noble state (high state) for which there is no corrosion and almost no change in self-potential even in the presence of chloride ions. Meanwhile, with the passivation film formed on the first electrode 3, even if the chloride ion concentration does not reach the boundary concentration at which carbon steel is corroded, local corrosion (pitting) occurs in the presence of chloride ions. Specifically, as shown in FIG. 9B, a deficit part 331 is formed on the passivation film 33 of the first electrode 3, and the part which has not undergone passivation of the first electrode 3 is exposed via the deficit part 331, and corrosion of the first electrode 3, specifically, gap corrosion of the first electrode 3 occurs. As a result, the self-potential of the first electrode 3 becomes less noble (decreases).

From such a fact, when chloride ions infiltrate the site to be measured, the difference in electric potential between the first electrode 3 and the second electrode 4 becomes greater. For that reason, it is possible to measure the change in chloride ion concentration of the site to be measured based on the difference in electric potential between the first electrode 3 and the second electrode 4.

Also, the pH of the concrete 101 in the concrete structure 100 gradually changes toward becoming acidic (neutralization) due to the effects of carbon dioxide, acidic rain, exhaust gas, and the like.

When the pH of the concrete 101 drops to as low as about 9, then, as illustrated in FIG. 9C, the passivation films 33 and 43 of the first electrode 3 and the second electrode 4 also begin to disintegrate, and the self-potential thereof drops (becomes less noble). At such a time, because the self-potentials of both the first electrode 3 and the second electrode 4 drop, the difference in electric potential between the first electrode 3 and the second electrode 4 is reduced. The difference in electric potential between the first electrode 3 and the comparative electrode 7, and the difference in electric potential between the second electrode 4 and the comparative electrode 7 respectively change sharply. For that reason, it is possible to detect with high precision the fact that the pH of the site to be measured became about 9. At such a time, each of the first electrode 3 and the second electrode 4 is undergoing progressive corrosion.

The use of such detection results makes it possible to monitor for a long time the temporal changes in the qualities of the concrete structure 100 after casting. For this reason, it is possible to become aware of the deterioration of the concrete 101 (neutralization or the intrusion of saline matter) before the reinforcing bars 102 are corroded. This makes it possible to paint the concrete structure 100 or perform repair work by a mixed anti-corrosion agent mortar or the like, before the reinforcing bars 102 are corroded.

It is also possible to determine whether or not there has been any abnormality during the casting of the concrete structure 100. For this reason, it is possible to prevent initial difficulties with the concrete structure 100, and to improve the quality of the concrete structure 100.

Second Example

The following is a description of the action of the sensor device 1 using a case where the first electrode 3 is composed of SUS304 and the second electrode 4 is composed of carbon steel (SD345).

In the concrete structure 100 immediately after casting, ordinarily, the concrete 101 exhibits a strong alkalinity when casting has been done appropriately. For this reason, at such a time, if chloride ions do not infiltrate the site to be measured, the same as with the first example described previously, as illustrated in FIG. 10A, a passivation film 33 is formed on the surface of the first electrode 3, and a passivation film 43 is formed on the surface of the second electrode 4. As a result, the difference in electric potential between the first electrode 3 and the second electrode 4 immediately after the concrete has been cast is reduced.

Thereafter, when chloride ions do not infiltrate the site to be measured of the concrete 101 of the concrete structure 100, and the pH of the concrete 101 drops to about 9, as illustrated in FIG. 10B, although the passivation film 33 of the first electrode 3 is stable and the self-potential thereof changes only slightly, the passivation film of the second electrode 4 begins to disintegrate, and thus the self-potential thereof drops (becomes less noble). The difference in electric potential between the first electrode 3 and the second electrode 4 is thereby sharply increased. As a result, it is possible to detect the fact that the pH of the site to be measured has reached about 9.

Note that when chloride ions infiltrate the site to be measured of the concrete 101 of the concrete structure 100 before the pH of the concrete 101 drops to about 9, the same as with the first example noted previously, the difference in electric potential between the first electrode 3 and the second electrode 4 becomes larger according to the chloride ion concentration.

Then, after the pH of the concrete 101 drops to about 9, when chloride ions infiltrate the site to be measured of the concrete 101 of the concrete structure 100, as shown in FIG. 10C, a deficit part 331 is formed piercing the passivation film 22 of the first electrode 3, so as to have gap corrosion of the first electrode 3 occur. As a result, the self-potential of the first electrode 3 becomes less noble (decreases). At this time, the self-potential for both the first electrode 3 and the second electrode 4 decreases, so the difference in electric potential between the first electrode 3 and the second electrode 4 becomes smaller. As a result, it is possible to detect that chloride ions have infiltrated the site to be measured.

With the sensor device 1 of the first embodiment like that described above, a local gap G is formed between the first electrode 3 and the gap forming member 8, so even in a state when the chloride ion concentration of the site to be measured is relatively low so that corrosion of the second electrode 4 due to chloride ions does not occur, it is possible to have corrosion of the first electrode 3 occur using gap corrosion. For that reason, even when the chloride ion concentration of the site to be measured is in a relatively low state, a difference in electric potential between the first electrode 3 and the second electrode 4 occurs, and it is possible to detect the infiltration of chloride ions based on this difference in electric potential.

Modification Example

Note that the mode of the through-groove 81 of the gap forming member 8 is not limited to the item described above, and for example it is possible to use a gap forming member having a through-groove or a through-hole such as that shown in FIGS. 11A, 11B and 11C instead of the gap forming member 8.

The gap forming member 8X1 shown in FIG. 11A has a plurality of through-grooves 81X1 extending in parallel to each other. The first electrode 3 of the sensor device 1X1 equipped with this kind of gap forming member 8X1 for example has a recess formed by etching with the gap forming member 8X1 as the mask, and as a result, a gap is formed for which gap corrosion of the first electrode 3 can occur.

The gap forming member 8X2 shown in FIG. 11B has a plurality of through-grooves 81X2 extending in parallel to each other in the direction orthogonal to the aforementioned through-grooves 81X1. The first electrode 3 of the sensor device 1X2 equipped with this kind of gap forming member 8X2 for example has a recess formed by etching with the gap forming member 8X2 as the mask, and as a result, a gap is formed for which gap corrosion of the first electrode 3 can occur.

The gap forming member 8X3 shown in FIG. 11C has a plurality of through-grooves 81X3 forming a shape that combines the aforementioned plurality of through-grooves 81X1 and the aforementioned plurality of through-grooves 81X2, in other words, forming a grid shape. The first electrode 3 of the sensor device 1X3 equipped with this kind of gap forming member 8X3 for example has a recess formed by etching with the gap forming member 8X3 as the mask, and as a result, a gap is formed for which gap corrosion of the first electrode 3 can occur.

Second Embodiment

The following is a description of a second embodiment of the present invention.

Figure 12:
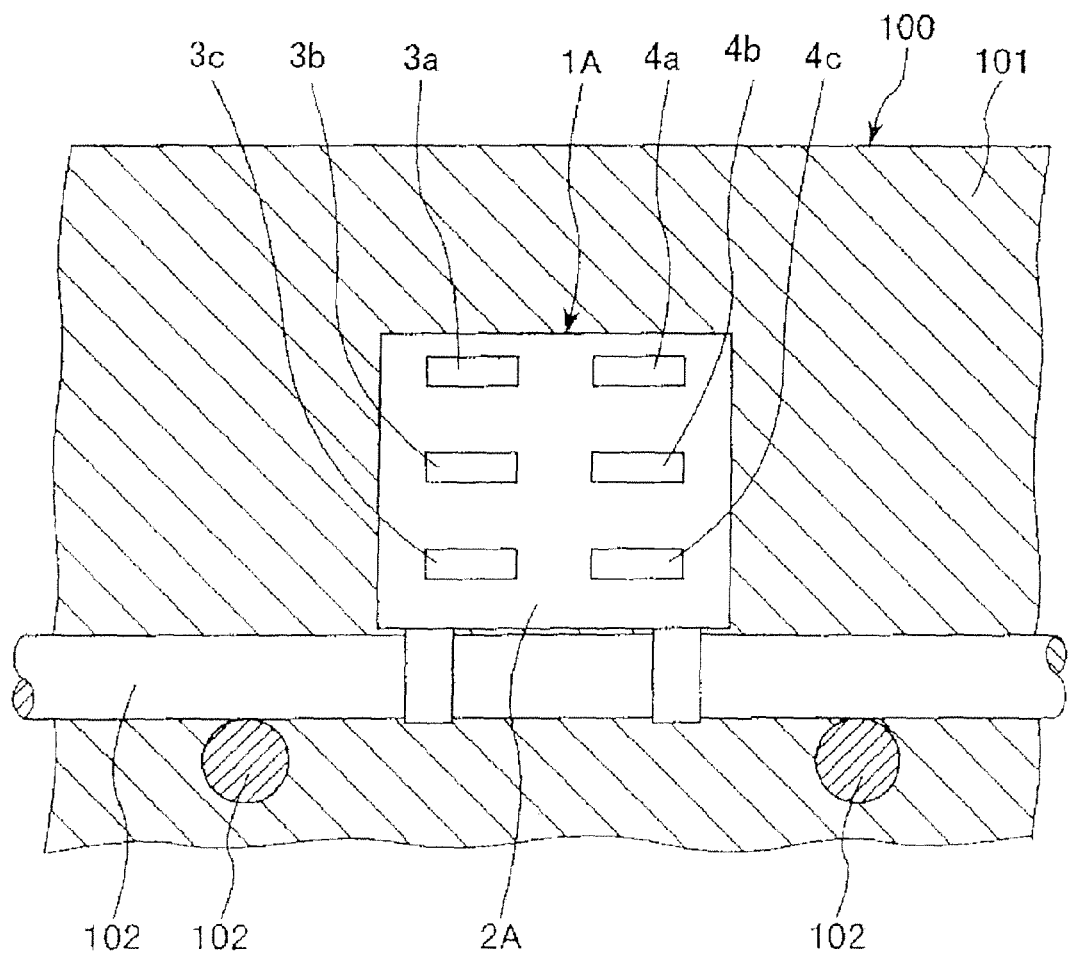
FIG. 12 is a drawing illustrating an example of the state of use of a sensor device according to a second embodiment of the present invention.

FIG. 12 is a drawing illustrating an example of the state of use of a sensor device according to a second embodiment of the present invention.

The following description of the second embodiment focuses on the points of difference with the embodiment described above, and omits a description of any similar matters.

The sensor device of the second embodiment is substantially similar to the sensor device of the first embodiment, except in that the number of the first electrode and the second electrode is different. Constituent elements which are similar to the embodiment described above have been assigned like reference numerals.

A sensor device sensor device 1A of this embodiment has a main body 2A, as well as a plurality of first electrodes 3a, 3b, 3c and a plurality of second electrodes 4a, 4b, 4c exposed to the surface of the main body 2A.

In this embodiment, the first electrodes 3a, 3b, 3c and the second electrodes 4a, 4b, 4c are provided mutually spaced apart. Also, the first electrodes 3a, 3b, 3c and the second electrodes 4a, 4b, 4c are each installed such that the electrode surface becomes perpendicular to or substantially perpendicular to the outer surface of the concrete structure 100.

The plurality of first electrodes 3a, 3b, 3c are all at mutually different distances from the outer surface of the concrete structure 100. Specifically, the plurality of first electrodes 3a, 3b, 3c are provided lined up in the stated order, from the outer surface of the concrete structure 100 inward.

Similarly, the plurality of second electrodes 4a, 4b, 4c are all at mutually different distances from the outer surface of the concrete structure 100. Specifically, the plurality of second electrodes 4a, 4b, 4c are provided lined up in the stated order, from the outer surface of the concrete structure 100 inward.

Furthermore, the first electrode 3a and the second electrode 4a are installed so as to both be equidistant from the outer surface of the concrete structure 100. The first electrode 3b and the second electrode 4b are installed so as to both be equidistant from the outer surface of the concrete structure 100. The first electrode 3c and the second electrode 4c are installed so as to both be equidistant from the outer surface of the concrete structure 100.

With such first electrodes 3a, 3b, 3c and second electrodes 4a, 4b, 4c, the first electrode 3a and the second electrode 4a form a pair, the first electrode 3b and the second electrode 4b form a pair, and the first electrode 3c and the second electrode 4c form a pair.

In the present embodiment, the sensor device 1A is configured such that the difference in electric potential between the first electrode 3a and the second electrode 4a, the difference in electric potential between the first electrode 3b and the second electrode 4b, and the difference in electric potential between the first electrode 3c and the second electrode 4c can each be measured by a functional element (not shown).

According to such a sensor device 1A according to the second embodiment, it is possible to accurately detect whether or not the pH and the chloride ion concentration of the installation environments of the first electrode 3a and the second electrode 4a, the installation environments of the first electrode 3b and the second electrode 4b, and the installation environments of the first electrode 3c and the second electrode 4c are at or below a prescribed value. That is, it is possible to accurately detect whether or not the pH at positions of different depths from the outer surface of the concrete structure 100 is at or below a prescribed value. This makes it possible to detect the speed at which the pH of the concrete 101 is changing toward being more acidic or the speed at which the chloride ion concentration is increasing. For this reason, it is possible to effectively predict the infiltration of neutralization or salt damage in the depth direction of the concrete structure 100.

Third Embodiment

Next, we will describe a third embodiment of the present invention.

Figure 13:
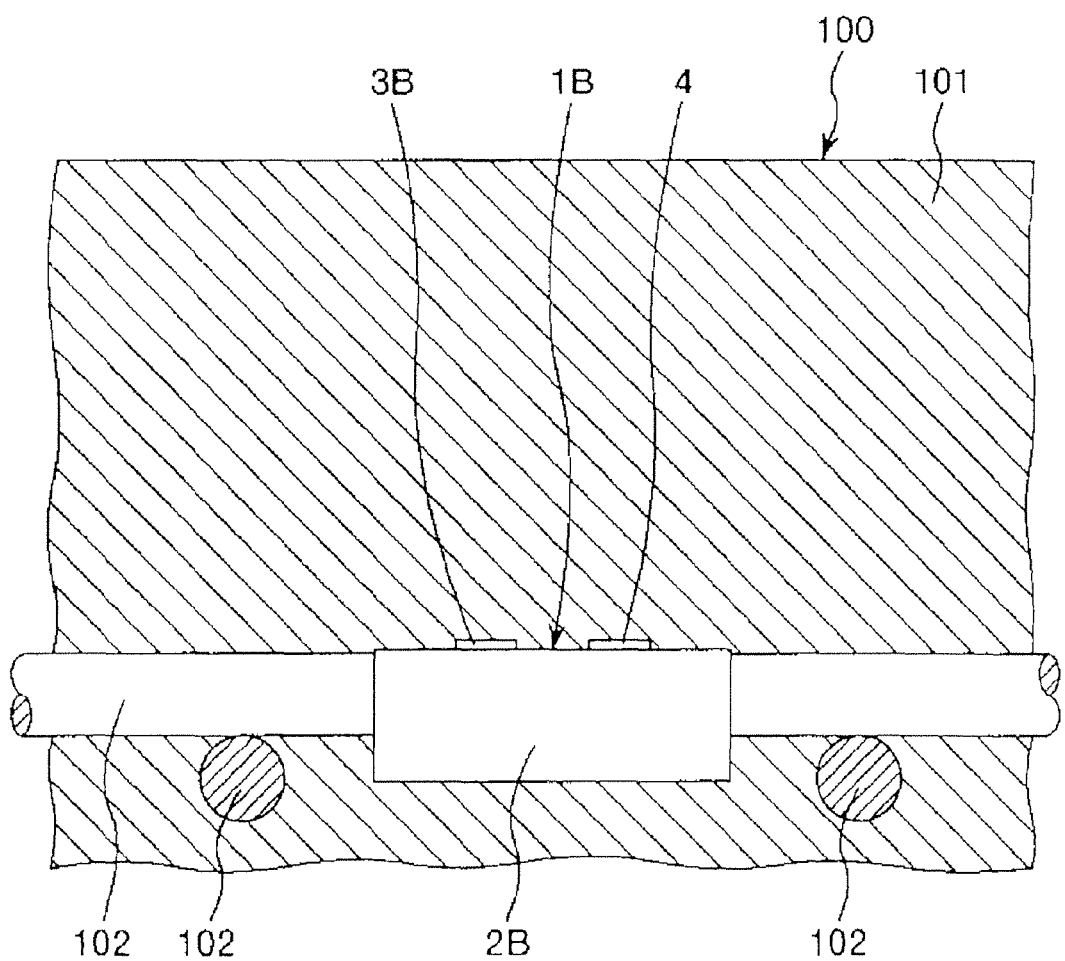
FIG. 13 is a drawing illustrating an example of the state of use of a sensor device according to a third embodiment of the present invention.
Figure 14:
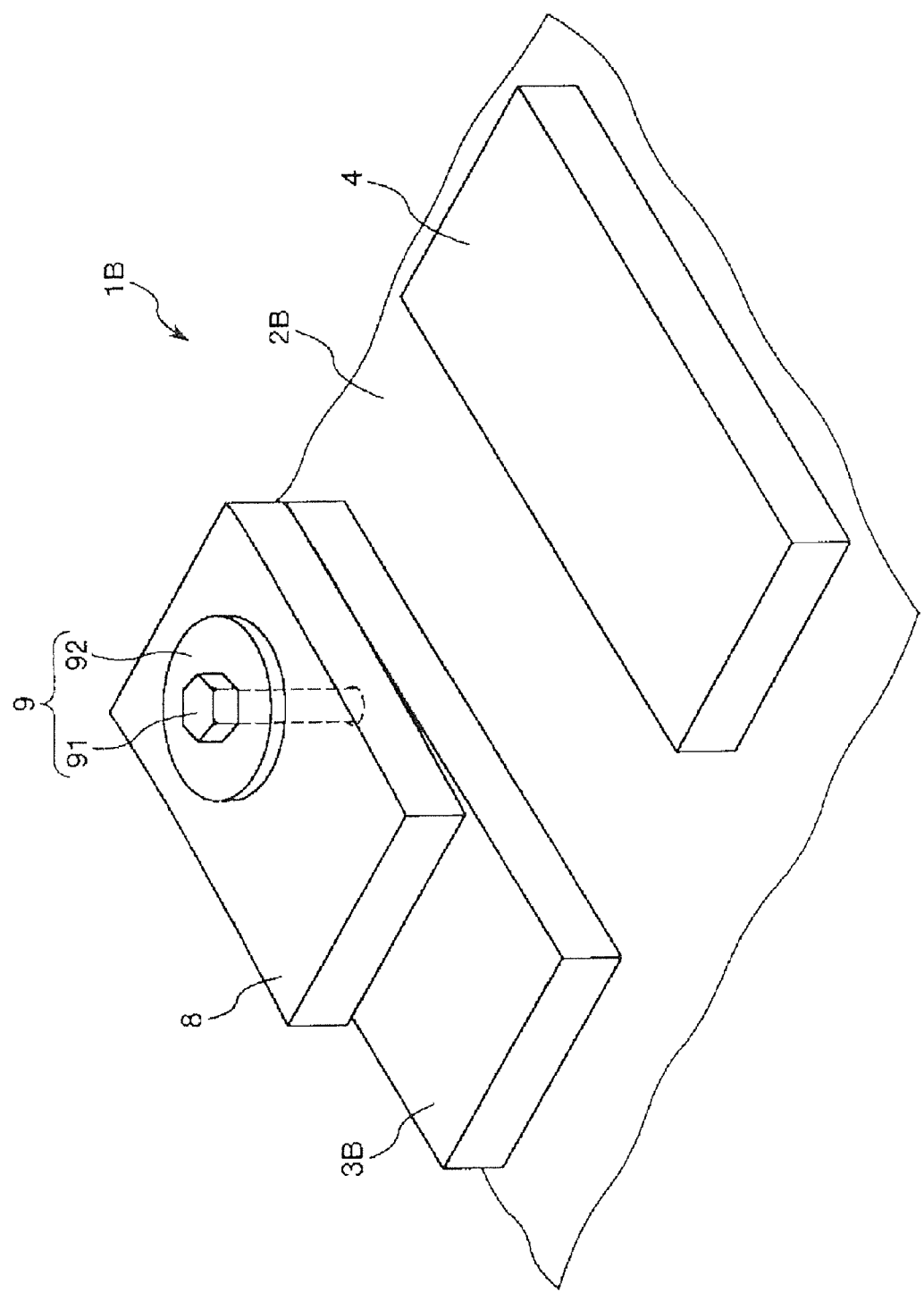
FIG. 14 is a perspective view for describing the first electrode, the second electrode, and the gap forming member illustrated in FIG. 13.
Figure 15:
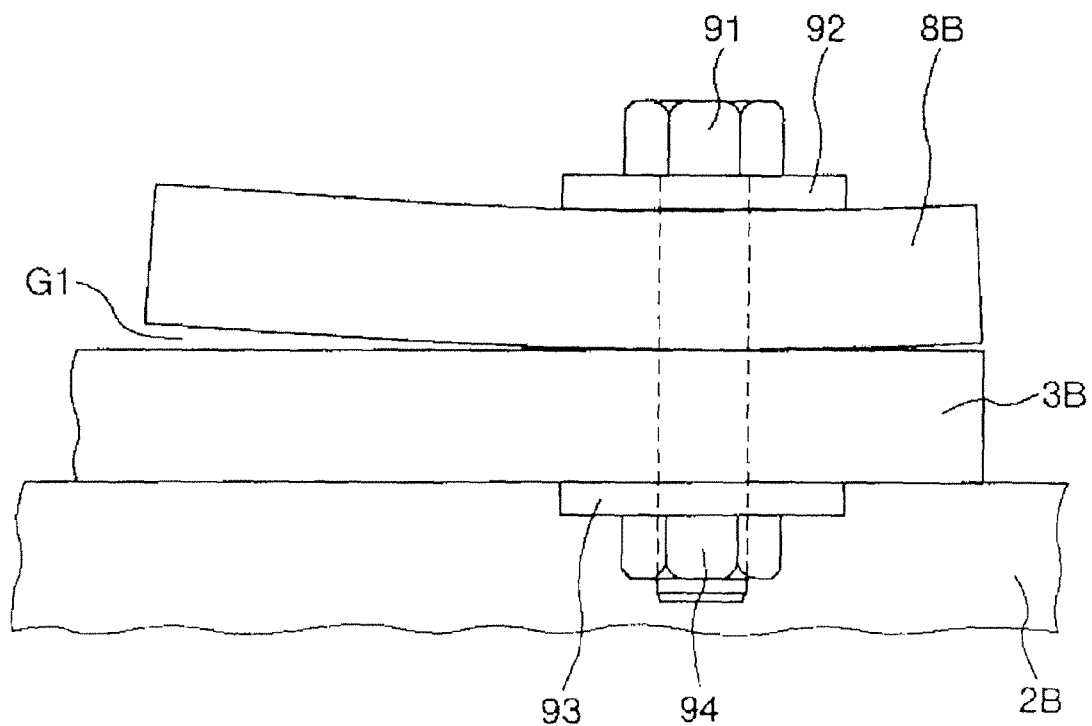
FIG. 15 is an enlarged side view illustrating the first electrode and the gap forming member illustrated in FIG. 14.

FIG. 13 is a drawing illustrating an example of the state of use of a sensor device according to a third embodiment of the present invention. FIG. 14 is a perspective view for describing the first electrode, the second electrode, and the gap forming member illustrated in FIG. 13. FIG. 15 is an enlarged side view illustrating the first electrode and the gap forming member illustrated in FIG. 14.

Following we will describe the third embodiment with a focus on the difference points from the previously described embodiments, and a description of items that are the same will be omitted.

The sensor device of the third embodiment is almost the same as the sensor device of the first embodiment except for a difference in the constitution of the first electrode and the gap forming member. Note that for like constitutions to those of the previously described embodiments, like reference numbers are used.

As shown in FIG. 13, the sensor device 1B of this embodiment has a main unit 2B, and a first electrode 3B and second electrode 4 provided on that main unit 2B.

Also, though omitted in FIG. 13 for convenience of illustration, as shown in FIG. 14, the sensor device 1B has a gap forming member 8B provided on the first electrode 3B.

With this embodiment, the first electrode 3B and the second electrode 4 are arranged so that the distance from the outer surface of the concrete structure 100 is almost the same as the distance between the outer surface of the concrete structure 100 and the reinforcing bars 102 (specifically, the covering depth of the reinforcing bars 102).

As shown in FIG. 14, the first electrode 3B and the second electrode 4 are respectively provided on the outer surface of the previously described main unit 2B.

As shown in FIG. 15, the gap forming member 8B is provide forming a gap G1 with a portion of the surface of the first electrode 3B.

With this embodiment, the gap forming member 8B forms a quadrangle with a plan view. Note that the plan view shape of the gap forming member 8B is not limited to being a quadrangle, and for example can also be a circular shape.

In particular, with this embodiment, the first electrode 3B and the gap forming member 8B each form a plate shape or a sheet shape, and in a state overlapping each other, the gap forming member 8B is fixed by a fixing member 9 to the first electrode 3. As a result, it is possible to easily and reliably form the gap G for which gap corrosion of the first electrode 3B can occur between the first electrode 3B and the gap forming member 8B.

To describe this in more detail, the fixing member 9 has a bolt 91, washers 92 and 93, and a nut 94.

Then, the first electrode 3B and the gap forming member 8B, in a mutually overlapping state, have a through-hole (not illustrated) formed that pierces both of them, the bolt 91 is inserted via the washer 92 from one side in the through-hole, and by screwing the nut 94 on the bolt 91 via the washer 93 from the other side, the gap forming member 8B is fixed to the first electrode 3B by the fixing member 9.

This kind of bolt 91 and nut 94 have the gap forming member 8B locally pressure welded to the first electrode 3B, so the part other than the pressure welded part of the gap forming member 8 slightly rises in relation to the first electrode 3B, and thus the gap G1 is formed. Note that the washers 92 and 93 can also be omitted.

The distance between the first electrode 3B and the gap forming member 8B at this gap G1 can be adjusted according to the tightening torque of the bolt 91 and the nut 94. Note that this distance can be set to the same size as the distance between the first electrode 3B and the gap forming member 8 at the gap G with the first embodiment described previously, specifically, the size for which gap corrosion of the first electrode 3B can occur.

With the sensor device 1B of the third embodiment like that described above as well, it is possible to distinguish between and measure the change in chloride ion concentration in the concrete 101 of the concrete structure 100 and the change in the pH of the concrete 101, and to use the resulting measurement information in planning the preservation of the concrete structure 100.

The preceding is a description of the sensor device of the present invention, based on the depicted embodiments, but the present invention is in no way limited thereto.

For example, the configuration of each of the parts in the sensor device of the present invention can be substituted with any desired configuration for exerting similar functions, and any desired configuration can be added.

Also, the embodiments described above are descriptions, by way of example, of a case where each of the first electrode and the second electrode is provided on the substrate, but there is no limitation thereto, and, for example, the first electrode and the second electrode may also be provided, for example, on the outer surface of the portion of the main body of the sensor device constituted of the sealing resin.

Further, the embodiments described above are descriptions, by way of example, of a case where the first electrode and the second electrode each form the shape of a thin film, but there is no limitation thereto, and the shapes of the first electrode and the second electrode may also each form, for example, a block shape, a wire shape, or the like. In the embodiments described above, the first electrode and the second electrode are each provided along the outer surface of the main body of the sensor device, but the first electrode and the second electrode may also each be projected out from the outer surface of the main body of the sensor device. In addition, the installation locations, size (relative sizes), and other aspects of the first electrode and the second electrode are also not limited by the embodiments described above, and may be as desired provided that measurement as described above is possible.

Also, the embodiments described above are descriptions, by way of example, of a case where the functional element has a CPU, an A/D conversion circuit, and a differential amplifier circuit, but there is no limitation thereto, and, for example, a ROM, RAM, various types of drive circuits, and other, additional circuits may be incorporated into the functional element.

The embodiments described above are descriptions, by way of example, of a case where information relating to the difference in electric potential between the first electrode and the second electrode is transmitted outside the sensor device by active tag communication by wireless transmission, but there is no limitation thereto, and, for example, passive tag communication may be used to transmit the information outside the sensor device, or the information may be transmitted outside the sensor device by wire.

The embodiments described above are descriptions, by way of example, of a case where the functional element 51, the power source 52, the temperature sensor 53, the communication circuit 54, the antenna 55, and the oscillator 56 are housed in the main body 2, and these [elements] are, together with the first electrode 3 and the second electrode 4, embedded in the concrete structure 100, which is the object to be measured, but the functional element 51, the power source 52, the temperature sensor 53, the communication circuit 54, the antenna 55, and the oscillator 56 may also be provided outside the object to be measured.

The second embodiment described above is a description, by way of example, of a case where a bolt and nut are used as the fixing members for fixing the gap forming member on the first electrode, but this is not limited thereto provided it is possible to fix the gap forming member to the first electrode while forming a gap for which gap corrosion of the first electrode 3 can occur.

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. A sensor device comprising:
a first electrode composed of a first metallic material;
a second electrode spaced apart from the first electrode, and composed of a second metallic material;
a gap forming member fixedly attached to a portion of a surface of the first electrode such that the gap forming member faces with the other portion of the surface of the first electrode to define a gap between the gap forming member and the other portion of the surface of the first electrode, the gap being connected to outside; and a functional element configured and arranged to measure a difference in electric potential between the first electrode and the second electrode so that a state of a measurement site to be measured is measured based on the difference in electric potential as measured by the functional element.

2. The sensor device according to claim 1, wherein each of the first metallic material and the second metallic material is a metallic material in which a passivation film is formed on a surface thereof or an existing passivation film on the surface thereof is eliminated in association with environmental changes in the measurement site.

3. The sensor device according to claim 2, wherein the first metallic material and the second metallic material are the same type of metallic material.

4. The sensor device according to claim 2, wherein the first metallic material and the second metallic material are different metallic materials.

5. The sensor device according to claim 2, wherein each of the first metallic material and the second metallic material is iron or an iron-based alloy.

6. The sensor device according to claim 1, wherein a recess is formed on the surface of the first electrode, and the gap forming member covers the recess with the gap being formed between a wall surface of the recess and the gap forming member, and includes a through-hole or through-groove connecting to the recess.

7. The sensor device according to claim 1, wherein each of the first electrode and the gap forming member has a plate shape or a sheet shape, and the gap forming member is fixed to the first electrode in a mutually overlapping state using a fixing member.

8. The sensor device according to claim 1, wherein the gap forming member is composed of a material with insulating properties.

9. The sensor device according to claim 1, wherein the gap forming member is composed of the same type of metallic material as the first metallic material.

10. The sensor device according to claim 1, wherein the gap forming member has alkaline resistant properties.

11. The sensor device according to claim 1, wherein a distance between the gap forming member and the first electrode at the gap is 1 μm or greater and 100 μm or less.

12. The sensor device according to claim 1, wherein the functional element is configured and arranged to detect whether or not a pH or a chloride ion concentration at the measurement site is at or below a prescribed value based on the difference in electric potential between the first electrode and the second electrode.

13. The sensor device according to claim 1, further comprising
an antenna, and
a communication circuit configured and arranged to provide power to the antenna,
the functional element being further configured and arranged to drive and control the communication circuit.

14. The sensor device according to claim 1, wherein the gap forming member has an edge portion that is spaced apart from the first electrode with the gap therebetween.

15. The sensor device according to claim 14, wherein the edge portion of the gap forming member defines an opening of the gap forming member through which the surface of the first electrode exposes outside.

16. A sensor device comprising:
a first electrode composed of a first metallic material;
a second electrode spaced apart from the first electrode, and composed of a second metallic material;
a gap forming member with a principal surface, the principal surface of the gap forming member being disposed on a portion of a principal surface of the first electrode with a gap therebetween, the gap being connected to outside; and
a functional element configured and arranged to measure a difference in electric potential between the first electrode and the second electrode so that a state of a measurement site to be measured is measured based on the difference in electric potential as measured by the functional element.

* * * * *